US012584164B2

(12) United States Patent
Dominguez-Nunez et al.

(10) Patent No.: US 12,584,164 B2
(45) Date of Patent: Mar. 24, 2026

(54) SYSTEM AND METHOD FOR DETECTING INHIBITION OF A BIOLOGICAL ASSAY

(71) Applicant: NEOGEN FOOD SAFETY US HOLDCO CORPORATION, Lansing, MI (US)

(72) Inventors: Wilfredo Dominguez-Nunez, Minneapolis, MN (US); Raj Rajagopal, Woodbury, MN (US); Nicholas A. Asendorf, St. Paul, MN (US); Saber Taghvaeeyan, Maple Grove, MN (US)

(73) Assignee: NEOGEN FOOD SAFETY US HOLDCO CORPORATION, Lansing, MI (US)

( * ) Notice: Subject to any disclaimer, the term of this patent is extended or adjusted under 35 U.S.C. 154(b) by 1073 days.

(21) Appl. No.: 17/612,037

(22) PCT Filed: May 15, 2020

(86) PCT No.: PCT/IB2020/054617
§ 371 (c)(1),
(2) Date: Nov. 17, 2021

(87) PCT Pub. No.: WO2020/234718
PCT Pub. Date: Nov. 26, 2020

(65) Prior Publication Data
US 2022/0220547 A1        Jul. 14, 2022

Related U.S. Application Data

(60) Provisional application No. 62/850,198, filed on May 20, 2019.

(51) Int. Cl.
*C12Q 1/6848*        (2018.01)
*C12Q 1/689*        (2018.01)
*G16B 40/00*        (2019.01)

(52) U.S. Cl.
CPC ........... *C12Q 1/6848* (2013.01); *C12Q 1/689* (2013.01); *G16B 40/00* (2019.02)

(58) Field of Classification Search
CPC .................. C12Q 1/6848; C12Q 1/689; C12Q 2600/142; C12Q 2531/113;
(Continued)

(56) References Cited

U.S. PATENT DOCUMENTS 6,733,645  B1        5/2004  Chow
2004/0197845  A1        10/2004  Hassibi
(Continued)

FOREIGN PATENT DOCUMENTS

WO        WO 1991-02817        3/1991
WO        WO 2004-062338        7/2004
(Continued)

OTHER PUBLICATIONS

Bar, "Kinetic outlier detection(KOD) in real-time PCR", Nucleic acids research, information retrieval Ltd., 2003, vol. 31, No. 17, pp. e105, 7 pages.
(Continued)

*Primary Examiner* — John McGuirk
(74) *Attorney, Agent, or Firm* — HYLTON-RODIC LAW PLLC

(57) ABSTRACT

In some examples, a system for detecting inhibition of a biological assay includes a detection device configured to amplify and detect a target nucleic acid. The detection device is configured to receive a sample comprising a matrix and a quantity of the target nucleic acid and to amplify the target nucleic acid within the sample over a nucleic acid amplification cycle. The detection device is configured to
(Continued)

capture a data set including measurements of the nucleic acid collected during the amplification cycle. The system further includes a computing device configured to receive the data set and to apply a machine-learning system to the data set to detect inhibited biological assays that tested negative for the target nucleic acid due to matrix inhibition.

12 Claims, 28 Drawing Sheets

(58) Field of Classification Search
CPC ........ C12Q 2531/119; C12Q 2531/143; G16B 40/00; G16B 25/20
See application file for complete search history.

(56) References Cited

U.S. PATENT DOCUMENTS

| | | | |
|---|---|---|---|
| 2007/0134652 A1 | 6/2007 | Slepnev | |
| 2009/0123935 A1* | 5/2009 | Jahan | C12Q 1/6851 |
| | | | 435/6.1 |
| 2011/0008785 A1 | 1/2011 | Tan | |
| 2017/0046480 A1* | 2/2017 | Almassian | G06F 18/214 |
| 2021/0010076 A1* | 1/2021 | Delubac | C12N 15/1089 |
| 2021/0241857 A1* | 8/2021 | Fraley | G16B 30/00 |

FOREIGN PATENT DOCUMENTS

| | | |
|---|---|---|
| WO | WO 2011-161186 | 12/2011 |
| WO | WO 2018-119443 | 6/2018 |
| WO | WO 2020-047081 | 3/2020 |

OTHER PUBLICATIONS

Dub, "A specific statistical model and algorithm related to the detection of mollicutes in contaminated biological samples by real-time transcription mediated amplification", Microbiol Methods, 2012, vol. 88, No. 2, pp. 248-254.
Hoorfar, "Making Internal Amplification Control Mandatory for Diagnostic PCR", Journal of Clinical Microbiology, vol. 41, No. 12, 2003, pp. 5835.
Hoorfar, "Practical Considerations in Design of Internal Amplification Controls for Diagnostic PCR Assays", Journal of Clinical Microbiology, 2004, vol. 42, No. 5, pp. 1863-1868.
Hyeon, "Development of multiplex real-time PCR with internal amplification control for simultaneous detection of Salmonella and Cronobacter in powdered infant powder", International Journal of Food Microbiology 2010, vol. 144, pp. 177-181.
Nau, "Substrate-Selective Supramolecular Tandem Assays: Monitoring Enzyme Inhibition of Arginase and Diamine Oxidase by Fluorescent Dye Displacement from Calixarene and Cucurbituril Macrocycles", J. Am. Chem. Soc., 2009, vol. 131, No. 32, pp. 11558-11570.
Oikonomou, "Selective PCR: a novel internal amplification control strategy for enhanced sensitivity in *Salmonella* diagnosis", Letters in Applied Microbiology, 2008, vol. 46, pp. 456-461.
Tichopad, "Quality control for quantitative PCR based on amplification compatibility test", Methods, Academics Press, 2010, vol. 50, No. 4, pp. 308-312.
Velez, "Massively parallel digital high resolution melt for rapid and absolutely quantitative sequence profiling", Scietific reports, 2017, vol. 7, No. 1, pp. 01-14.
XP55715711.
International Search report for PCT International Application No. PCT/IB2020/054617 mailed on Jul. 24, 2020, 6 pages.

* cited by examiner

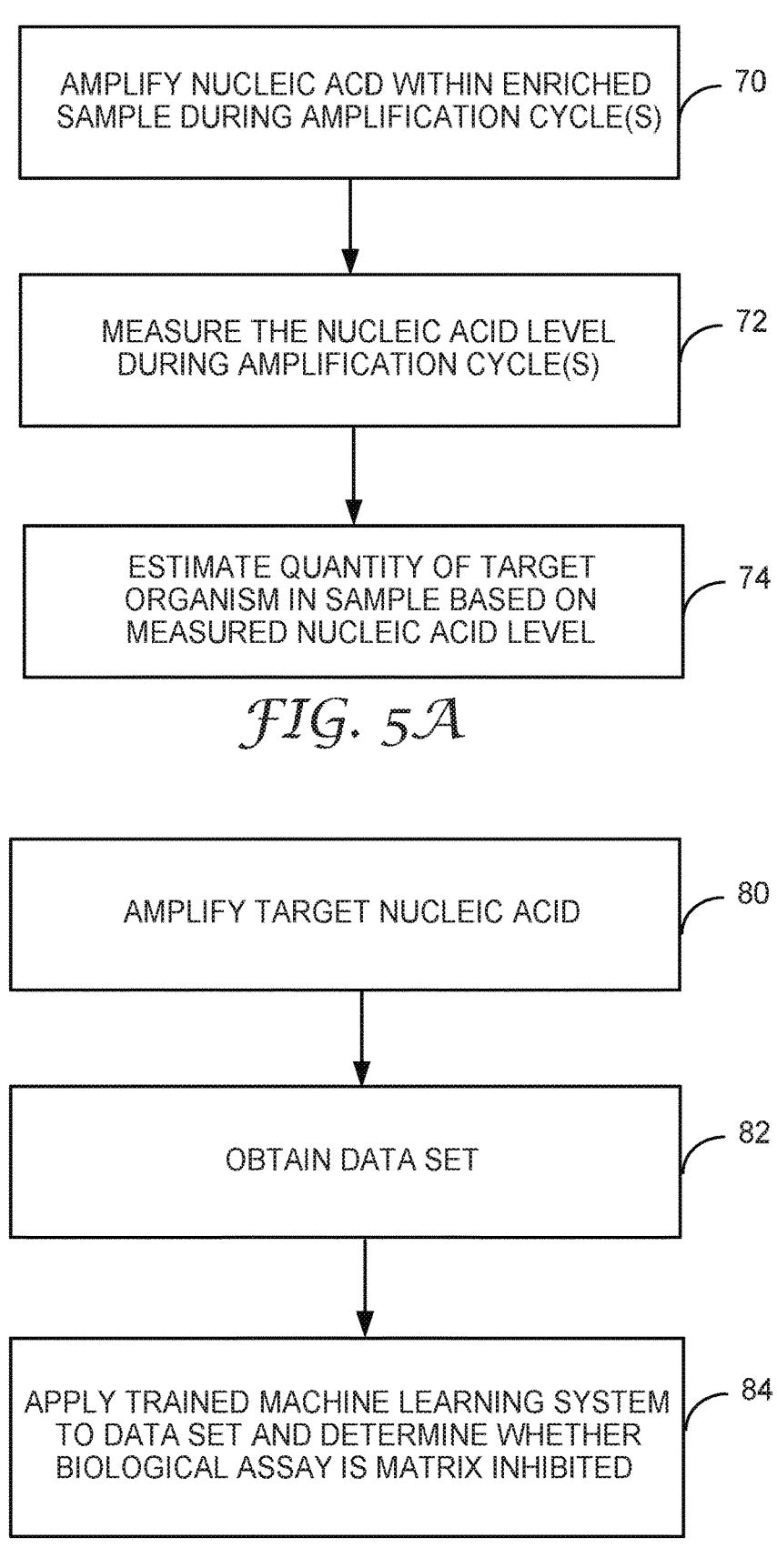

AMPLIFY NUCLEIC ACD WITHIN ENRICHED
SAMPLE DURING AMPLIFICATION CYCLE(S) — 70

MEASURE THE NUCLEIC ACID LEVEL
DURING AMPLIFICATION CYCLE(S) — 72

ESTIMATE QUANTITY OF TARGET
ORGANISM IN SAMPLE BASED ON
MEASURED NUCLEIC ACID LEVEL — 74

*FIG. 5A*

AMPLIFY TARGET NUCLEIC ACID — 80

OBTAIN DATA SET — 82

APPLY TRAINED MACHINE LEARNING SYSTEM
TO DATA SET AND DETERMINE WHETHER
BIOLOGICAL ASSAY IS MATRIX INHIBITED — 84

*FIG. 5B*

LABEL EACH DATA SE  T AS ONE OF FALSE NEGATIVE OR TRUE NEGATIVE — 150

TRAIN A MACHINE LEARNING SYSTEM WITH THE LABELED DATA SETS — 152

DETECT INHIBITION OF AN ASSAY AND ISSUE A RESULT USING THE TRAINED MACHINE LEARNING SYSTEM — 154

SYSTEM AND METHOD FOR DETECTING INHIBITION OF A BIOLOGICAL ASSAY

CROSS REFERENCE TO RELATED APPLICATIONS

This application is a national stage filing under 35 U.S.C. 371 of PCT/IB2020/054617, filed 15 May 2020, which claims the benefit of U.S. Provisional Application No. 62/850,198, filed 20 May 2019, the disclosures of which are incorporated by reference in their entireties herein.

TECHNICAL FIELD

This disclosure relates to systems and methods for detecting inhibition of biological assays, and, in particular, to systems and methods for detecting whether a biological assay is inhibited.

BACKGROUND

Foodborne bacterial infections and diseases are an ongoing threat to public health. Regulatory agencies such as the United States Department of Agriculture's Food Safety and Inspection Service respond to this threat by promulgating pathogen-reduction performance standards for pathogens (e.g., *Salmonella* and *Campylobacter*) in food, feed, water, and corresponding processing environments.

Food, feed, and water producers use quantitative and/or qualitative techniques to determine the quantity and/or presence of microorganisms, such as bacterial pathogens, in food, feed (e.g., animal feed), water and in corresponding processing environments. Such producers may, for instance, perform quantitation of total and indicator bacteria to assess the effectiveness of pathogen-intervention processes such as hazard analysis and critical control points (HACCP)-based food safety procedures and other hygiene control measures. These same producers may perform threshold tests for target organisms at other points of the process, issuing an indication of whether a sample tested positive or negative for the target organism.

Typically, people seeking to determine the quantity of a pathogen rely on traditional methods of quantitation, such as most probable number (MPN) estimates based on serial culture dilution. Such approaches are often time consuming, tedious, and error-prone. Biological assays such as DNA/RNA amplification, using reporters such as bioluminescence or fluorescence, on the other hand, are used to determine if a sample tested positive or negative for the target organism.

SUMMARY

The disclosure provides systems for detecting inhibition of a biological assay (e.g., a particular sample of food, feed, water, or corresponding environmental sample) being evaluated to detect the presence of and/or to quantify one or more target organisms using nucleic acid amplification assays. The disclosure also provides systems and methods for training a machine learning system to detect inhibited biological assays and to issue a result indicating whether the biological assay is inhibited.

An example system for detecting inhibition of a biological assay includes a detection device configured to amplify and detect a target nucleic acid associated with a target organism during the biological assay, the detection device comprising a reaction chamber configured to receive a sample comprising a matrix and a quantity of the target nucleic acid and to amplify the target nucleic acid within the sample over a nucleic acid amplification cycle; and a detector, the detector configured to capture, during the nucleic acid amplification cycle, measurements representative of a quantity of the target nucleic acid present in the sample and to store the measurements in a data set. The detection device further including a machine learning system configured to receive the data set, wherein the machine-learning system includes processing circuitry trained to detect biological assays inhibited due to matrix inhibition.

In one example, a method includes receiving a plurality of data sets, wherein each data set is associated with a biological assay, each data set including measurements, performed on the associated biological assay by a nucleic acid amplification device of a specified type and collected over at least a portion of a nucleic acid amplification cycle, of a target nucleic acid detected within the associated biological assay, wherein the target nucleic acid is associated with a target organism. The method further includes labeling, as false negative data sets, those data sets from the plurality of data sets that are associated with biological assays that tested negative for the target nucleic acid due to matrix inhibition and that would have tested positive had matrix inhibition not been present and labeling, as true negative data sets, those data sets from the plurality of data sets that are associated with biological assays that correctly tested negative for the target nucleic acid. The method further includes training a machine-learning systems with the true negative and false negative data sets to detect biological assays that tested negative for the target nucleic acid due to matrix inhibition.

An example non-transitory computer-readable medium storing instructions that, when executed by processing circuitry, cause the processing circuitry to receive a data set generated by amplifying and detecting a target nucleic acid associated with a target organism in a sample comprising a matrix and a quantity of the target nucleic acid over a nucleic acid amplification cycle, the data set including measurements representative of the quantity of the target nucleic acid present in the sample and to store the measurements in a data set, wherein the data set includes; and apply a machine-learning system to the data set. The machine-learning technique is trained to detect inhibited biological assays and to issue a result indicating whether the biological assay tested negative for the target nucleic acid due to matrix inhibition.

An example non-transitory computer-readable medium stores instructions that, when executed by processing circuitry, cause the processing circuitry to establish a machine-learning system trained to detect matrix-inhibited biological assays; receive a data set generated by amplifying and detecting a target nucleic acid associated with a target organism in a sample comprising a matrix and a quantity of the target nucleic acid over a nucleic acid amplification cycle, the data set including measurements representative of the quantity of the target nucleic acid present in the sample; determine, by applying the machine-learning system to the data set, whether the data set is from a matrix-inhibited sample; and label the data set accordingly.

Thus, in the systems and methods described herein, the data resulting from a biological assay may be collected and analyzed using machine learning systems, such as support vector machines, boosted decision trees, systems, and/or others. Such data may be used to train and build machine learning systems for particular pathogens and/or matrices. The machine learning systems, trained with one or more proper data sets, can examine much or all of a signal response in molecular diagnostic assays (e.g., qPCR and/or LAMP). Such machine-learning systems, trained with the proper data set, can examine a background response of a nucleic acid-based molecular diagnostic assay and compute the probability that the background signal corresponds to a matrix that is rendering the assay unable to produce a positive reaction (i.e., is inhibited). Enabling the identification of false-negative results may help improve effectiveness of pathogen-intervention processes used during food production relative to molecular methods that do not include the application of such trained machine-learning systems.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIG. 5A is a flow diagram illustrating an example technique for estimating a quantity of the target organism in a sample, in accordance with one aspect of the disclosure.

FIG. 5B is a flow diagram illustrating an example technique for detecting inhibition of a biological assay, in accordance with one aspect of the disclosure.

DETAILED DESCRIPTION

Figure 1:
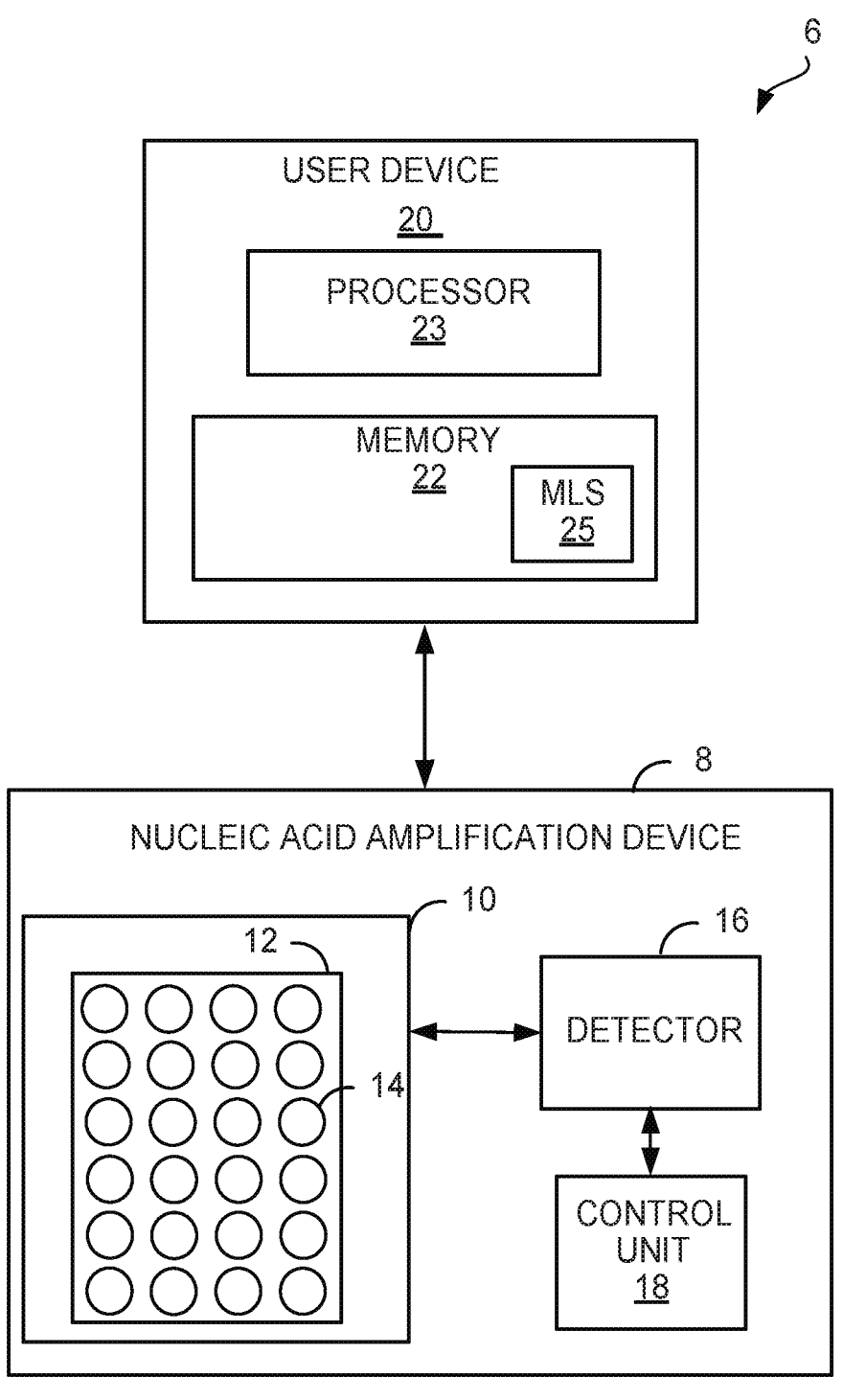
FIG. 1 is a block diagram illustrating an example system that includes a nucleic acid amplification device configured to amplify and detect a target nucleic acid and a user device configured to receive data from the nucleic acid amplification device and to apply a machine-learning system to the data, in accordance with aspects of the disclosure.

Molecular methods are increasingly used to detect the presence of and quantity of target organisms in a sample. Assays based on molecular methods such as nucleic acid amplification ((e.g., LAMP or PCR) are highly efficient. They can, however, be affected by the presence of matrix-derived substances which can interfere or prevent the reaction from performing correctly, a process termed inhibition. In food production, matrix-derived substances, such as spices and environmental samples, may act as inhibitors that can interfere with nucleotide amplification assays such as PCR and LAMP, leading to false negative results.

It can be difficult to eliminate inhibition. Careful sample treatment may be used, for instance, to remove inhibitory substances. No sample treatment, however, can be relied on to completely remove inhibitory substances.

Amplification controls may also be used to control for inhibition. Such controls may be used, for instance, to verify that the assay has performed correctly. Typically, an internal amplification control (IAC) is a non-target DNA sequence present in the very same reaction as the sample or target nucleic acid extract. If it is successfully amplified to produce a signal, any non-production of a target signal in the reaction is considered to signify that the sample did not contain the target pathogen or organism. If, however, the reaction produces neither a signal from the target nor the IAC, it signifies that the reaction has failed, signally the absence of the target organism when, in fact, the target organism is present (i.e., a "false negative"). Detection of false negatives during the amplification cycle may be, therefore, critical for reliable testing.

The addition of amplification controls adds complexity and cost to molecular methods. It would be advantageous to eliminate the use of amplification controls when applying molecular methods to detect or quantify target organisms in a sample, even in the face of inhibition. Approaches for detecting false negatives in inhibited samples are, therefore, presented below. These approaches may, for instance, be used to detect false negatives in nucleotide amplification without the need for internal or external amplification controls.

In the following discussion, the term "food" also includes beverages. The term "water" includes drinking water, but the term "water" also includes water used in other situations that require detection of or quantitative measurement of one or more of the microorganisms in the water.

As noted above, food, feed and water producers use quantitative and/or qualitative techniques to determine the quantity and/or presence of microorganisms, such as bacterial pathogens, in food, feed (e.g., animal feed), water and corresponding processing environments. Quantitative techniques are used, for instance, to assess the effectiveness of pathogen-intervention processes used during food production. Such analysis may lead to more effective risk analyses and to the development of more effective ways to reduce the level of pathogens in the food, feed and water supply.

Molecular methods (e.g., LAMP or PCR) may be used to detect the presence of and quantity of target organisms in a sample. These methods are routinely used for detecting presence/absence of pathogens (qualitative) and offer faster results (1 day) than traditional culture-based methods (3-5 days). Such methods may also be used to quantitate pathogens extracted from a sample, as discussed below. Molecular methods of pathogen quantification provide results more quickly than more traditional methods (e.g., in hours rather than one or more days). They also are not limited to quantification of total bacteria and indicator bacteria, but also may be used to quantify specific bacteria, yeast, mold, or other pathogens.

An advantage of molecular methods is that amplification occurs at a predictable rate given appropriate conditions. For instance, qPCR is widely used as a molecular method for detecting a variety of bacteria. qPCR may also be used for the absolute quantification of pathogens present in a given amount of sample. Standard curves containing known amounts of the target DNA (plasmids, genomic DNAs or other nucleic acid molecules) are run in parallel with the unknown samples. Based on the standard curve, the efficiency of the reaction and the dilution steps used for the nucleic acid extraction and analysis, the absolute number of pathogens in the unknown samples may be estimated. In these types of analysis, linear regression models are used, the efficiency of amplification becomes critical and standards need to be run with every run, adding to cost, time, possible contamination of samples. Furthermore, the standard curve approach has limited use when cell counts (not DNA) are being used. For these reasons, traditional methods of determining the quantity of a pathogen in a sample remain in use.

However, to improve detection sensitivity, it may be advantageous to have single target rather than multianalyte detection, since reagents can compete leading to incomplete amplification of targets and hence inaccurate results. Some of the newly developed techniques such as LAMP are robust, use simple detection technologies allowing more ease of use and simpler instruments.

Pathogen detection as discussed below includes both qualitative and quantitative detection. The following disclosure further describes systems and methods for training and using machine learning systems in molecular methods of pathogen detection, thereby improving the accuracy of pathogen detection and for quantification assays, reducing or eliminating the need for preparing and using standard curves with every run. In some example methods described herein, LAMP bioluminescent assays and/or PCR assays (e.g., qPCR assays) may be used in a training run to amplify a target nucleic acid (e.g., a nucleic acid associated with a target organism) present in a sample in a known initial quantity and to detect light generated within the sample during amplification of the target nucleic acid. In other example methods described herein, assays such as nicking-enzyme amplification reaction (NEAR), helicase-dependent amplification (HDA), nucleic acid sequence-based amplification (NASBA), or transcription-mediated amplification (TMA) assays may be used in a training run to amplify a target nucleic acid (e.g., a nucleic acid associated with a target organism) present in a sample in a known initial quantity and to provide measurements corresponding to amplification of the known initial quantity of the target organism.

Any suitable variation on such assays may be used. Variations on a traditional LAMP assay that may be used may include colorimetric LAMP (cLAMP) assays, in which pH changes driven by the accumulation of protons during LAMP can be visualized via observation of color changes of a pH-sensitive colorimetric dye that occur with nucleic acid amplification. Other such variations may include turbidity-LAMP assays, in which formation of magnesium pyrophosphate during LAMP results in turbidity that increases in correlation with nucleic acid yield and that can be quantified in real-time. Materials and methods used in such variations on traditional LAMP assays, and/or on PCR assays, may be understood by those of skill in the art and thus are not described in detail here. It should be understood that example nucleic acid amplification techniques and variations thereon described herein are not intended to be limiting. Instead, any suitable nucleic acid amplification technique may be used in the techniques described herein, such as in a training run to amplify a target nucleic acid.

Data from the training run may be fed into a machine learning system to train the machine learning system. The trained machine learning system then may be used to detect presence/absence of target organism and/or estimate an unknown initial quantity of the target organism present in a sample, such as a food sample, feed sample, water or environmental sample from a food or feed processing environment.

In example methods described herein, LAMP biolumi-nescent assays and/or PCR assays (e.g., qPCR assays) may be used in a training run to amplify a target nucleic acid (e.g., a nucleic acid associated with a target organism) present in a series of samples with known inhibitors/matri-ces of nucleic acid amplification assays, determine inhibi-tion using dilution of the samples and/or use of an internal or external amplification control. The method collects data for each sample representative of light generated within the sample during amplification of the target nucleic acid and associates the collected data with presence/absence of target organisms and/or known quantities of the target nucleic acid, or with known quantities of the organism being detected.

In other example methods described within, LAMP bio-luminescent assays and/or PCR assays (e.g., qPCR assays) may be used in a training run to amplify a target nucleic acid (e.g., a nucleic acid associated with a target organism) present in a series of samples having known initial quantities of the target organism. The method collects data for each sample representative of light generated within the sample during amplification of the target nucleic acid and associates the collected data with known quantities of the target nucleic acid, or with known quantities of the organism being detected.

Data from the training run is then fed into a machine learning system to train the machine learning system. The trained machine learning system may then be used to determine inhibition or not of the target organism present in a sample, such as a food sample, feed sample, water or environmental sample from a food or feed processing envi-ronment.

In yet other example methods described within, LAMP bioluminescent assays and/or PCR assays (e.g., qPCR assays) may be used to obtain data corresponding to samples collected from a particular environment (e.g., a poultry processing plant or a cheese factory). The samples are reviewed using traditional presence/absence and/or quanti-tation methods and each sample is labeled with the value determined via one or more of the traditional methods. The data from the labeled samples is then fed into a machine learning system to train the machine learning system for that particular environment. The trained machine learning sys-tem may then be used to better determine presence/absence and/or estimate an unknown initial quantity of the target organism and/or nucleic acid present in a sample, such as a food sample, feed sample, water or environmental sample from the particular environment.

It should be noted that while in some examples nucleic acids associated with a target organism may be described herein as being DNA, in other examples, a nucleic acid associated with a target organism may be an RNA. In such other examples, an amplification technique such as quanti-tative reverse transcription PCR (RT-qPCR) and reverse transcription LAMP (RT-LAMP) on total RNA or mRNA of a sample may be used in a method of training a machine learning system to estimate an initial quantity of a target organism in a sample and/or in applying such a trained machine learning system.

Each machine learning system is based on at least one model. The model may be a regression model based on techniques such as, for example, support vector regression, random forest regression, linear regression, ridge regression, logistic regression, Lasso, or nearest neighbor regression. Or the model may be a classification model based on techniques such as, for example, support vector machines, decision tree and random forest, linear discriminant analysis, neural net-works, nearest neighbor classifier, stochastic gradient descent classifier, gaussian process classification, or naïve bayes. Both types of models rely on the use of labeled data sets to train the model.

Samples from food, feed, water and corresponding pro-cessing environments may include a matrix that includes material, such as carbohydrates, lipids, proteins, pigments, spices, and/or other components of the food, feed, water or environment from which the sample was obtained. Some such matrices inhibit or prevent the amplification of a target nucleic acid, such as by preventing the polymerase from extending the nucleic acid in the time allowed, thereby producing incomplete amplification products and hindering accurate detection and/or quantification of the target organ-ism. This problem is termed "matrix inhibition."

In samples having a matrix that includes one or more inhibitors, nucleic acid amplification and detection assays may provide a false-negative result even though the sample does include an amount of the target organism that should have resulted in detection of the target organism. Although dilution of a sample may help alleviate the inhibitory effect of a matrix that includes one or more inhibitors, dilution may also cause loss of signal associated with the target nucleic acid if the initial quantity of the nucleic acid preset in the sample was relatively low.

The following disclosure, therefore, also describes sys-tems and methods for detecting matrix inhibition of biologi-cal assays and systems and methods for training and using machine learning systems to detect matrix inhibition of biological assays. The described systems and methods improve the accuracy of pathogen detection and quantifica-tion (e.g., by reducing or eliminating the occurrence of false-negative results of such biological assays).

In some examples, the systems and methods for training and using machine-learning systems to detect matrix inhi-bition of biological assays include systems and methods that distinguish between biological assays that correctly test negative for the target nucleic acid (i.e., "true negative" biological assays) and biological assays that tested negative for the target nucleic acid due to matrix inhibition but that would have tested positive had matrix inhibition not been present (i.e., "false negative" biological assays). Such an approach may reduce or eliminate the need for the use of internal and/or external controls with nucleic acid amplifi-cation and detection methods to detect such inhibition. In some such example approaches, experts review biological assays identified during the nucleic acid amplification cycle as negative for the target organism, labeling each biological assay as either a true negative or a false negative. Measure-ments recorded during the nucleic acid amplification cycle for each biological assay are then used to train a machine learning system to distinguish between biological assays that are truly negative and those that would test positive but for matrix inhibition.

As noted above, matrices in food samples, environmental samples, blood, fecal samples, may include inhibitors that prevent the amplification/binding of the analyte. Often an internal control is employed to monitor the inhibition. In assays using a single reporter molecule and assays that do not enable multiplex capability, an external control may be used to monitor such inhibition. Biological assays such as DNA/RNA amplification, immunoassays, using reporters such as bioluminescence, fluorescence, or colorimetry, usu-ally have an intrinsic background. The intrinsic background may be used to calibrate the assays. The background or baseline portions of the reporter signal in nucleic acid-based molecular diagnostic assays may be, for instance, the prod-uct of unbound fluorescent probes, free dye, probe cleavage, matrix interference with the signal, instrument calibration and other factors. As such, these background or baseline signals are often subtracted from or otherwise suppressed in the reporter signal provided to a user during nucleic acid amplification assays because they contain little information relevant to the detection or quantification of the target organism. In some examples, however, systems and methods for training machine-learning systems use the intrinsic background and/or baseline portions of the reporter signal to detect matrix inhibition.

Examples are provided below for LAMP-bioluminescent assays. LAMP-bioluminescent assays use bioluminescence at a single wavelength and do not allow multiplex capability. However, the assays have inherent bioluminescence background, and, in some examples, this background is utilized to train a machine learning system to predict matrix inhibition of the assays. Such an approach provides a mechanism for detecting whether the matrix has an inhibitory effect and, therefore, for preventing false negative outcomes.

Thus, systems and methods described herein may utilize an otherwise unused inherent background or baseline portion of a reporter signal to train and use a machine-learning system to distinguish inhibited biological assays from non-inhibited biological assays in nucleic acid amplification and detection techniques with which internal controls for inhibition may not be usable. For example, one or more data sets from one or more corresponding training runs may be fed into a machine-learning system to train the machine-learning system. In some examples, it may be sufficient to include in such training runs samples for which a false-negative result was determined and samples for which a negative result correctly was determined. It may not be necessary to train the machine-learning system with samples for which a positive result was determined, which may simplify a method of training the machine-learning system. In some such examples, the machine-learning system may be trained to detect biological assays that tested negative for the target nucleic acid due to matrix inhibition and that would have tested positive for the target nucleic acid had matrix inhibition not been present.

The trained machine-learning system then may be used to detect inhibited biological assays and to issue a result indicating whether the biological assay tested negative for the target nucleic acid due to matrix inhibition. In contrast with systems and methods that rely upon internal or external controls for detection of inhibition, the example systems and methods described herein may address the issue of inhibition detection by using an otherwise unused inherent background or baseline portion of a reporter signal, which may reduce cost and/or time needed for pathogen detection or quantification and/or increase throughput of such assays.

FIG. 1 is a block diagram illustrating an example system that includes a nucleic acid amplification device configured to amplify and detect a target nucleic acid associated with a target organism and a user device configured to receive data from the nucleic acid amplification device and to apply a machine-learning system to the data, in accordance with aspects of the disclosure. Nucleic acid amplification device 8 is configured to amplify and detect a target nucleic acid, in accordance with one aspect of the disclosure. Nucleic acid amplification device 8 includes a reaction chamber 10 configured to amplify the target nucleic acid. In one example approach, as shown in FIG. 1, reaction chamber 10 includes a block 12 that may be heated and/or cooled via a heat source such as a Peltier system. As illustrated in FIG. 1, block 12 defines a plurality of wells 14, each of which may be dimensioned to receive a reaction vessel, which may be any suitable plastic tube configured for use in nucleic acid amplification assays. Nucleic acid amplification device 8 further includes a detector 16 and a control unit 18. Detector 16 may be configured to capture light within reaction chamber 10 under control of control unit 18. For example, detector 16 may be configured to capture a data set including time-series measurement samples of light emitted by a light-emitting species within sample contained within a reaction vessel received within one of wells 14 during one or more nucleic acid amplification cycles. In some examples, the sample may include a target nucleic acid and the light-emitting species, the latter of which may emit light in a stoichiometric relationship with the target nucleic acid such that the light emitted by the light-emitting species increases with an increase in the quantity of replicated target nucleic acid in the sample.

In some examples, nucleic acid amplification device 8 may be any suitable nucleic acid amplification device configured for LAMP (e.g., traditional LAMP assays, or cLAMP, turbidity LAMP, or other variations on traditional LAMP assays). In examples in which light is emitted by a light-emitting species captured by detector 16, the light may be bioluminescence, fluorescence or light of any visible color. In examples in which a turbidity LAMP technique is used, the detector may measure at least one of absorbance, transmittance, or reflectance. Additionally, or alternatively, nucleic acid amplification device 8 may be any suitable nucleic acid amplification device configured for qPCR or any other nucleic acid amplification technique (e.g., NEAR, HDA, NASBA, TMA, or others). In some such other examples, light emitted by the light-emitting species and captured by detector 16 may be fluorescence.

In some of the example methods described herein for training machine-learning systems, nucleic acid amplification device 8 may be a nucleic acid amplification device of a specified type. For example, nucleic acid amplification device 8 may include one or more specific features and/or may be a specific model of a nucleic acid amplification device from a specified manufacturer. In some such examples, a trained machine learning system resulting from such methods may be tailored to the specified type of nucleic acid amplification device, which may enhance the accuracy of the trained machine learning system. Nucleic acid amplification devices having any suitable configuration may be used. For example, a nucleic acid amplification device may include a rack (e.g., a spinning rack) configured to receive reaction vessels instead of a block. In some such examples, the reaction vessels may be capillaries or more traditionally-configured tubes. In some examples, a detector 16 of a nucleic acid amplification device may be position above the reaction vessels or in any suitable position. Thus, the configuration of nucleic acid amplification device described herein is not intended to be limiting but to illustrate an example.

The example system of FIG. 1 further includes user device 20, which may include a processor 23 and a memory 22 used to store parameters representing one or more trained machine learning systems 25. In one example approach, user device 20 receives a data set from control unit 18 for each sample tested. In some such example approaches, each data set includes data representing measurements of a reporter signal captured by a device 8 during the amplification cycle of the given sample. In some example approaches, the measurements include measurements of a quantity of light received by detector 16 at specific times during the amplification cycle of the given sample. As further discussed below with respect to FIG. 3, user device 20 may be a device such as a computer workstation, tablet, or other such user device co-located with nucleic acid amplification device 8 in a user's laboratory. Nucleic acid amplification device 8 may be configured to transmit the data set from control unit 18 to user device 20, such as via any suitable wired connection (e.g., metal traces, fiber optics, Ethernet, or the like), a wireless connection (e.g., personal area network, local area network, metropolitan area network, wide area network, a cloud-based system, or the like), or a combination of both. For example, user device 20 may include a communications unit that includes a network interface card, such as an Ethernet card, an optical transceiver, a radio frequency transceiver, a Bluetooth® interface card, WiFi™ radios, USB, or any other type of device that can send and receive information to and from nucleic acid amplification device 8.

In some example approaches, processor 23 may be configured to apply a trained machine-learning system 25 stored in memory 22 to the data set to detect inhibited biological assays and to issue a result indicating whether the biological assay tested negative for the target nucleic acid due to matrix inhibition. Additionally, or alternatively, processor 23 may be configured to apply a trained machine-learning system (i.e., trained learning system 25 or another trained machine-learning system stored in memory 22) to a data set to estimate a quantity of a target organism present in the biological assay as a function of the data set. In some examples, processor 23 may store the result indicating whether the biological assay tested negative for the target nucleic acid due to matrix inhibition and/or the estimated quantity of the target organism, such as in association with other data pertaining to the biological assay. In examples in which processor 23 is configured to apply a trained machine-learning system to a data set to estimate a quantity of the target organism, the estimated quantity may be compared to a corresponding threshold value in a limit test to determine whether the sample passes or fails the limit test. The threshold value may, in some such example approaches, be a value associated with one or more regulatory standards, industry practices, or associated intervention processes. For example, the estimated quantity of the target organism in a sample may help enable evaluation of effectiveness of intervention procedures designed to improve process efficiency and/or reduce pathogen levels in food products, feed products, water and/or corresponding preparation environments.

In examples in which a processor (e.g., processor 23) is configured to apply a trained machine-learning system to a data set associated with an amplified sample of a target nucleic acid to estimate a quantity of the target organism in the sample may help address public health issues associated with pathogens. For example, since the systems and methods for nucleic acid quantitation described herein provide quantity values more quickly than traditional approaches to pathogen quantitation, such systems and methods may make pathogen quantitation more accessible to the food industry. This increased accessibility may be used by the food industry, for instance, to obtain a more nuanced understanding of pathogen presence than can be obtained simply by detecting the presence or absence of the pathogen. The increased accessibility may also be used to support limit testing in pathogen analysis, as one goal of limit testing is to detect foodborne pathogen concentrations that meet or exceed a threshold concentration and limit the release of products that may negatively impact public health.

In this manner, the systems and methods described herein that include applying a trained machine learning system to a data set associated with an amplified sample of a target nucleic acid to detect and/or quantify inhibited biological assays and to issue a result indicating whether the biological assay tested negative for the target nucleic acid due to matrix inhibition may help address public health issues associated with pathogens. Detection of false-negative results (e.g., results that incorrectly indicate a target nucleic acid is not present or not present at a threshold level) of biological assays inhibited due to matrix inhibition as described herein may help protect consumer health, such as by limiting the consumer exposure to potentially contaminated products.

Figure 2:
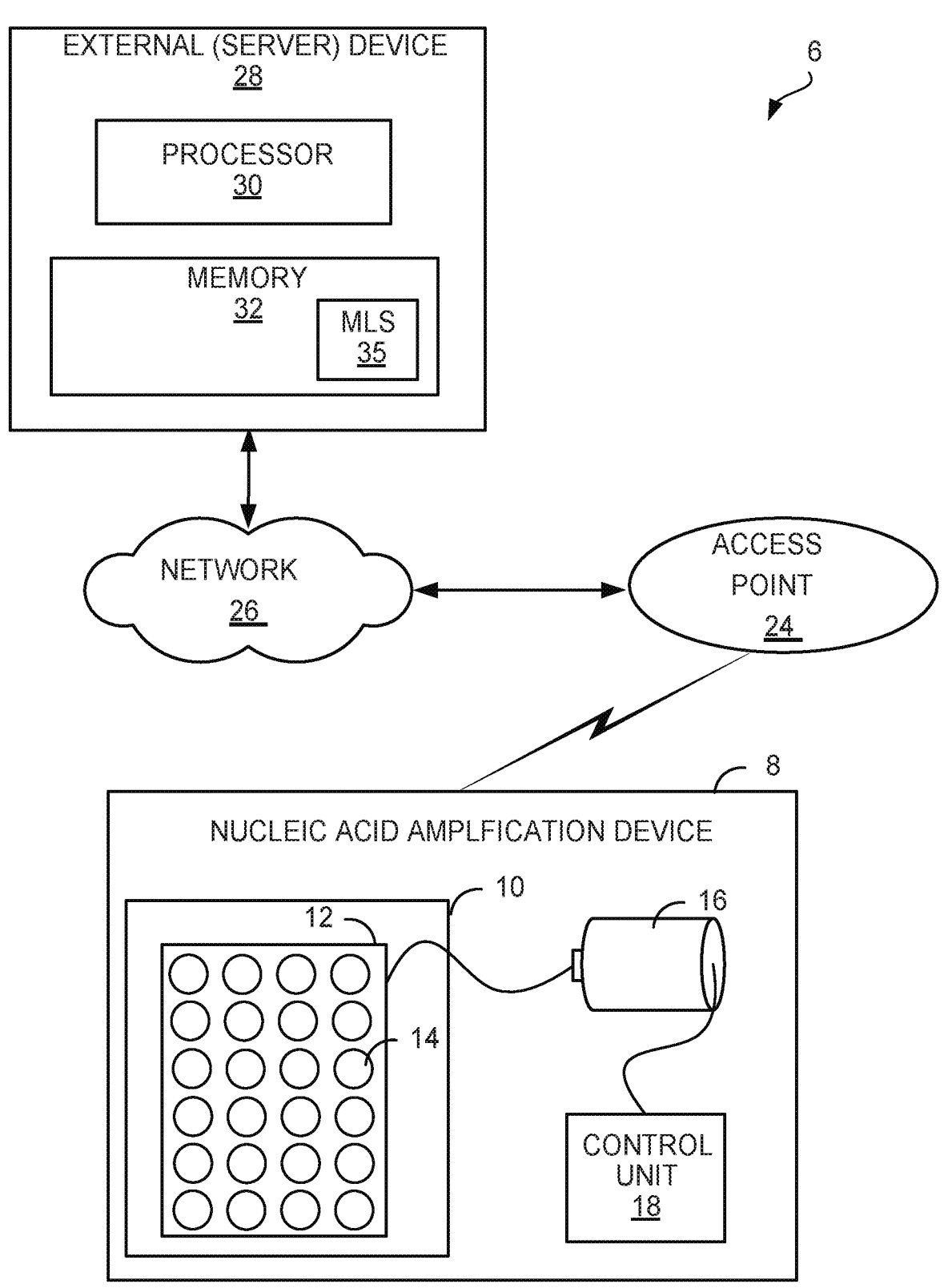
FIG. 2 is a block diagram illustrating an example system that includes an external device, such as a server, and an access point coupled to the nucleic acid amplification device of FIG. 1 via a network, in accordance with one aspect of this disclosure.

FIG. 2 is a block diagram illustrating an example system 6 that includes an external device 28, such as a server, and an access point 24 coupled to the nucleic acid amplification device 8 of FIG. 1 via a network 26, in accordance with one aspect of this disclosure. In one example, as shown in FIG. 2, system 6 may include an access point 24, a network 26, and one or more external devices, such as an external device 28 (e.g., a server), which may include a memory 32 and/or processing circuitry 30. In the example shown in FIG. 2, nucleic amplification device 8 may use communication circuitry (not shown) used to communicate with access point 24 via a wireless connection. Access point 24 then conveys the information received from nucleic amplification device 8 to external device 28 through network 26 via a wired connection and conveys the information received from external device 28 through network 26 to nucleic amplification device 8 via the wireless connection.

Access point 24 may comprise a processor that connects to network 26 via any of a variety of connections, such as telephone dial-up, digital subscriber line (DSL), or cable modem, or other suitable connections. In other examples, access point 24 may be coupled to network 26 through different forms of connections, including wired or wireless connections. In some examples, access point 24 may be a user device, such as a computer workstation or tablet that may be co-located with nucleic amplification device 8 and the user. Nucleic amplification device 8 may be configured to transmit data to access point 24, such as data sets described above with respect to FIG. 1. In addition, access point 24 may interrogate nucleic amplification device 8, such as periodically or in response to a command from a user or from network 26, in order to retrieve data sets pertaining to one or more biological assays, or to retrieve other information stored in a memory (not shown) of nucleic amplification device 8. Access point 24 may then communicate the retrieved data to external device 28 via network 26.

In some examples, memory 32 of external device 28 may be configured to provide a secure storage site for data collected from access point 24 and/or nucleic acid amplification device 8. In some examples, memory 32 stores parameters representing one or more trained machine learning systems 35. In some examples, external device 28 may assemble the data in web pages or other documents for viewing by users via access point 24 or one or more other computing devices of the system of FIG. 2. In this manner, the system of FIG. 2 may enable remote (e.g., cloud-based) storage and access of data associated with a user's testing of food or feed products and/or of corresponding production environments. Such systems may be customized to meet a particular user's data storage and/or access needs.

In some examples, memory 32 of external device 28 may be configured to provide a secure storage site for data collected from access point 24 and/or nucleic acid amplification device 8. In some examples, external device 28 may assemble data in web pages or other documents for viewing by users via access point 24 or one or more other computing devices of the system of FIG. 2. In this manner, the system of FIG. 2 may enable remote (e.g., cloud-based) storage and access of data associated with a user's testing of food or feed products and/or of corresponding production environments. Such systems may be customized to meet a particular user's data storage and/or access needs.

Figure 3:
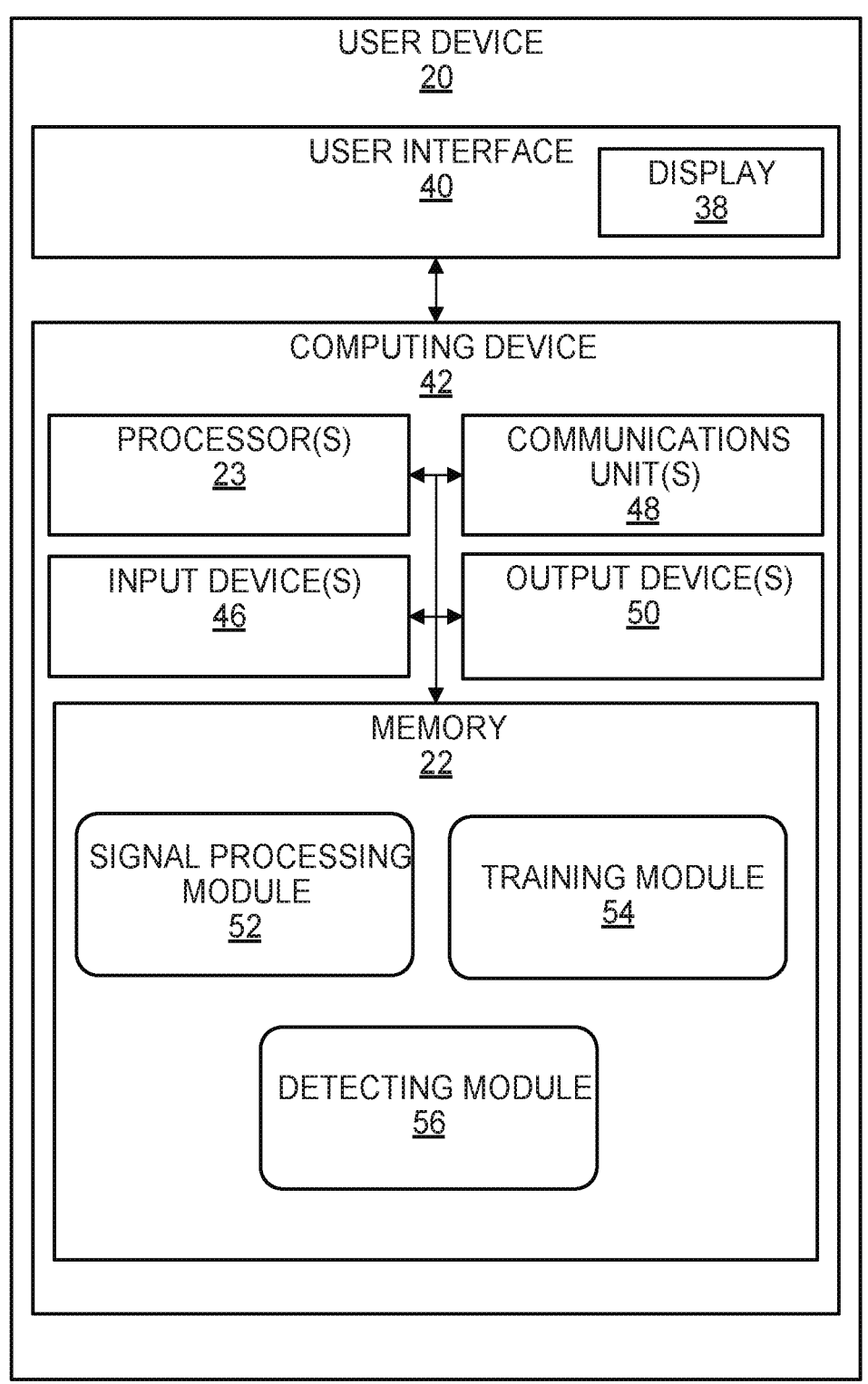
FIG. 3 is a schematic and conceptual diagram illustrating the example user device of FIG. 1, in accordance with one aspect of the disclosure.

FIG. 3 is a schematic and conceptual diagram illustrating features of user device 20 of FIG. 1, in accordance with one aspect of the disclosure. Although FIG. 3 is described with respect to user device 20 of FIG. 1, one or more components of user device 20 described herein may be functionally and/or structurally similar to one or more components of access point 24 and/or external device 28 illustrated in FIG. 2. In one example approach, user device 20 includes user interface 40 and computing device 42. User interface 40 may include display 38, a graphical user interface (GUI), a keyboard, a touchscreen, a speaker, a microphone, or the like.

One or more processors 23 of computing device 42 are configured to implement functionality, process instructions, or both for execution within computing device 42. For example, processors 23 may be capable of processing instructions stored within memory 22, such as instructions for applying a trained machine-learning system to a data set to detect inhibited biological assays and to issue a result indicating whether the biological assay tested negative for the target nucleic acid due to matrix inhibition and/or apply a trained machine-learning system to a data set to estimate an initial quantity of a target nucleic acid or a target organism present in a sample. Examples of one or more processors 23 may include, any one or more of a microprocessor, a controller, a digital signal processor (DSP), an application specific integrated circuit (ASIC), a field-programmable gate array (FPGA), or equivalent discrete or integrated logic circuitry.

In some examples, computing device 42 may utilize one or more communications units 48 to communicate with one or more external devices (e.g., external device 28 of FIG. 2 and/or nucleic acid amplification device 8) via one or more networks, such as one or more wired or wireless networks. Communications units 48 may include a network interface card, such as an Ethernet card, an optical transceiver, a radio frequency transceiver, or any other type of device configured to send and receive information. Communications units 48 may also include WiFi™ radios or a Universal Serial Bus (USB) interface.

In some examples, one or more output devices 50 of computing device 42 may be configured to provide output to a user using, for example, audio, video or tactile media. For example, output devices 50 may include display 38 of user interface 40, a sound card, a video graphics adapter card, or any other type of device for converting a signal into an appropriate form understandable to humans or machines, such as a signal associated with information pertaining to a status, outcome, or other aspect of one or more data sets resulting from amplification cycles carried out by nucleic acid amplification device 8 analyzed by a trained machine learning system. In some example approaches, user interface 40 includes one or more of output devices 50 employed by computing device 42.

Memory 22 of computing device 42 may be configured to store information within computing device 42 during operation. In some examples, memory 22 may include a computer-readable storage medium or computer-readable storage device. Memory 22 may include a temporary memory, meaning that a primary purpose of one or more components of memory 22 may not necessarily be long-term storage.

Memory 22 may include a volatile memory, meaning memory 22 does not maintain stored contents when power is not provided thereto. Examples of volatile memories include random access memories (RAM), dynamic random-access memories (DRAM), static random-access memories (SRAM), and other forms of volatile memories known in the art. In some examples, memory 22 may be used to store program instructions for execution by processors 23, such as instructions for applying a trained machine-learning system to a data set received from nucleic acid amplification device 8 via one or more communications units 48. Memory 22 may, in some examples, be used by software or applications running on computing device 42 to temporarily store information during program execution.

In some examples, memory 22 may further include a signal processing module 52, a training module 54, and a detecting module 56. In some such examples, detecting module 56 includes a machine learning system (such as machine learning systems 25 of FIGS. 1 and 35 of FIG. 2) that, when trained and applied to a data set, detects inhibited biological assays and issues a result indicating whether the biological assay tested negative for a target nucleic acid due to matrix inhibition and/or estimates the concentration of target organisms in a sample. In one such example approach, training module 54 receives data sets of assays with known cell concentrations collected by a nucleic acid amplification device 8 over one or more amplification cycles and uses the data sets to train detecting module 56 to estimate the concentration of target organisms in a sample.

In some examples, memory 22 may include non-volatile storage elements. Examples of such non-volatile storage elements include magnetic hard discs, optical discs, floppy discs, flash memories, or forms of electrically programmable memories (EPROM) or electrically erasable and programmable (EEPROM) memories. In one such example approach, signal processing module 52 may be configured to analyze data received from nucleic acid amplification device 8, such as a data set captured by detector 16 and comprising time-series measurement samples of the light emitted by light-emitting species within a sample during an amplification cycle, and process the data to improve the quality of the sensor data.

Computing device 42 may also include additional components that, for clarity, are not shown in FIG. 3. For example, computing device 42 may include a power supply to provide power to the components of computing device 42. Similarly, the components of computing device 42 shown in FIG. 3 may not be necessary in every example of computing device 42.

Figure 4:
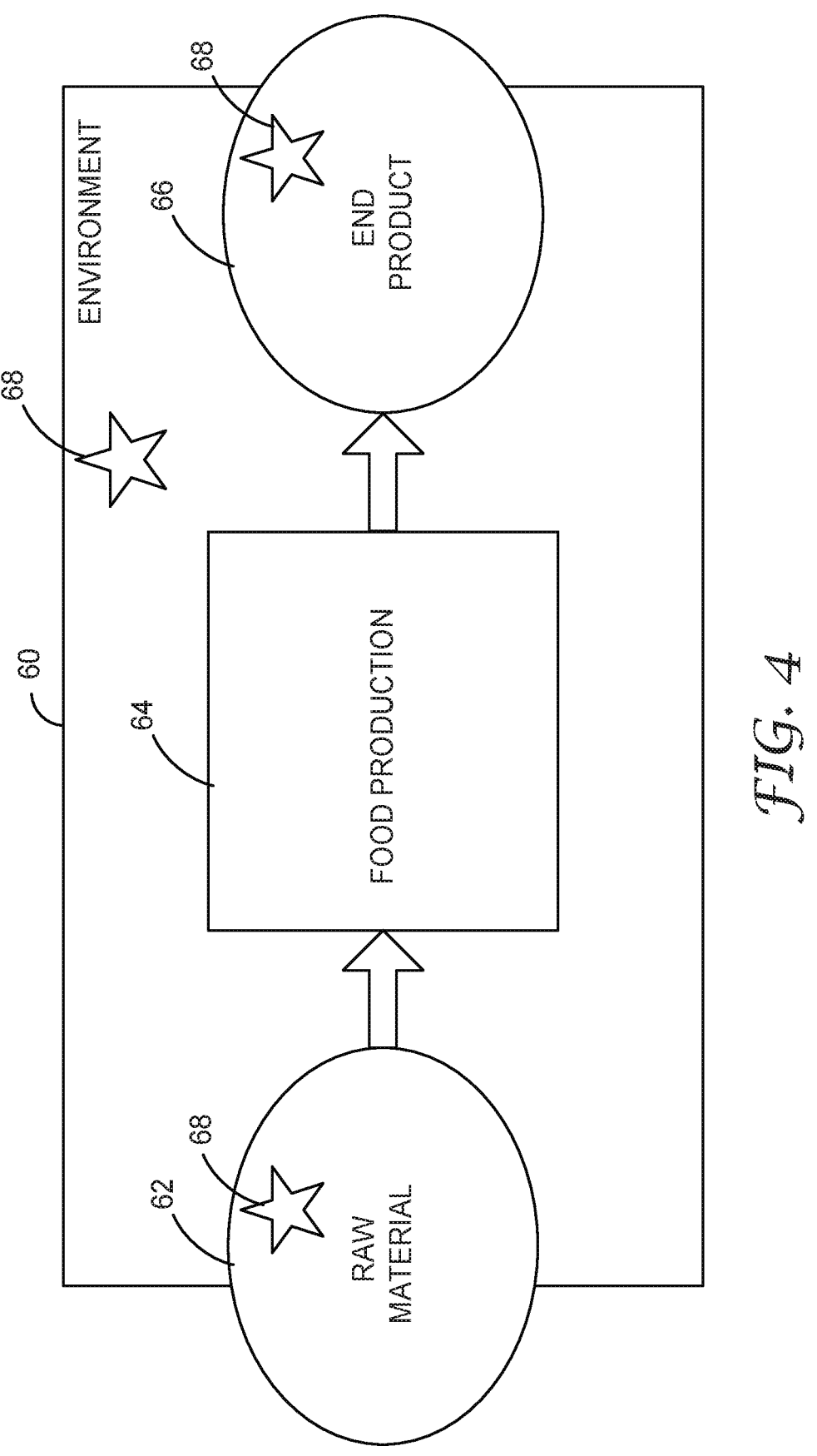
FIG. 4 is a flow diagram illustrating example points for pathogen testing before, during, and/or after food, feed, or water production, in accordance with one aspect of the disclosure.

FIG. 4 is a flow diagram illustrating example points for pathogen testing before, during, and/or after food or feed production, in accordance with one aspect of the disclosure. As illustrated in FIG. 4, food production environment 60 may include raw material 62. Food production processes 64 that process raw material 62 and produce end product 66 may take place within food production environment 60. In some examples, production processes 64 may take place entirely within food production environment 60, whereas raw material 62 may enter food production environment 60 from outside of food production environment 60 at the beginning of the processes illustrated in FIG. 4. In some examples, food production environment 60 may be an environment in which food or feed materials are harvested, such as a greenhouse or field in which such materials are grown. In some examples, samples from food production environment 60 may be water samples from water sources within the food production environment 60, such as sources of water used for washing and/or cooking.

Raw material 62 may acquire pathogens from outside food production environment 60 and introduce such pathogens into food production environment 60 as or after raw material 62 is introduced into food production environment 60. Thus, to help reduce foodborne illness caused by pathogens, there is an increased trend in pathogen testing of raw materials (e.g., raw material 62) and food production environments (e.g., food production environment 60). Moreover, pathogen testing of raw material 62 may help prevent pathogen contamination of end product 66 (or of other end products) by identifying contamination before raw material enters food production environment 60 such that entrance of contaminated raw materials into food production environment 60 may be avoided.

End product 66 may be located within environment 60 for a period of time prior to shipment out of environment 60, such as before, during, and after packaging. End product 66 may acquire pathogens from food production environment 60, such as pathogens introduced by raw material 62 or from other sources within food production environment 60. However, as discussed above, traditional methods of pathogen detection and/or quantification may be significantly time consuming, taking one or more days to yield results, and molecular methods of pathogen detection and/or quantification have not yet gained widespread use. In some instances, the time required for traditional methods may limit food processing rates. Moreover, due to the time requirement, such traditional methods provide pathogen assessment only as current as the time the sample was taken, which may not provide an accurate assessment of a current state of a material, environment, or product. Thus, at least due to the time advantage of the molecular methods for pathogen detection, quantification, and or inhibition detection described herein, pathogen testing of raw material 62, food production environment, and/or end product 66 (e.g., as part of a release test), such as at test points 68, according to such methods that may provide more up-to-date assessments, which ultimately may help prevent the release of contaminated end products to the public.

FIG. 5A is a flow diagram illustrating an example technique for estimating a quantity of the target organism in a sample, in accordance with one aspect of the disclosure. The example approach of FIG. 5A may be carried out using a nucleic acid amplification device such as nucleic acid amplification device 8 of the systems of FIGS. 1 and 2. As described above with respect to FIG. 1, nucleic acid amplification device 8 may be a nucleic acid amplification device of any suitable type and may be configured to carry out any suitable nucleic acid amplification technique, such as LAMP or PCR. Although described in the context of the systems of FIG. 1, the example technique of FIG. 5A may be carried out using any suitable nucleic acid amplification device and computing device. Systems and methods for estimating a quantity of a target organism in a sample are described in further detail in MACHINE LEARNING QUANTIFICATION OF TARGET ORGANISMS USING NUCLEIC ACID AMPLIFICATION ASSAYS, filed herewith, the description of which is incorporated herein by reference.

In the example approach of FIG. 5A, nucleic acid amplification device 8 amplifies a target nucleic acid within an enriched sample within reaction chamber 10 (70). In some examples, the sample may be derived from food production environment 60, raw material 62 or end product 66 as described above with respect to FIG. 4. Nucleic acid extracted from the sample may be placed within a reaction vessel (e.g., a PCR tube) along with a light-emitting species that emits light in a stoichiometric relationship with the target nucleic acid, which may be a DNA sequence associated with a target organism (e.g., a bacterial genus or species). In some examples, the sample may be an enriched sample derived from a sample of food or feed raw material, end product, water or production environment. For example, the sample placed in the reaction vessel may be an enriched sample from a culture derived from the initial sample. In some such examples, the estimated quantity of the organism may be an estimated initial quantity of the organism. In some examples, the reaction vessel containing a sample and a light-emitting species collectively may be referred to herein as a "biological assay." Detector 16 of nucleic acid amplification device captures a data set comprising time-series measurement samples of the light emitted by the light-emitting species over one or more amplification cycles and transmits the data set to computing device 42 of user device 20, a computing device of access point 24, or any other suitable computing device (72).

In the example of user device 20, one or more of processors 23, signal processing module 52, and/or other components of computing device 42 may apply a trained machine learning system to the data set to estimate the quantity of the target organism in the sample (74). In some examples, the data set may include one or more data subsets associated with one or more different portions or phases of the amplification cycle, such as one or more portions or phases before, during, and/or after a peak amplitude of light emitted over the amplification cycle. Including data subsets from such different portions or phases of the amplification cycle may contribute to the accuracy with which the trained machine learning system may estimate the quantity of the target organism in the sample, as further described below with respect to FIGS. 11 and 12.

FIG. 5B is a flow diagram illustrating an example technique for detecting inhibited biological assays, in accordance with one aspect of the disclosure. The example approach of FIG. 5B may be carried out using a nucleic acid amplification device such as nucleic acid amplification device 8 of the systems of FIGS. 1 and 2. As described above with respect to FIG. 1, nucleic acid amplification device 8 may be a nucleic acid amplification device of any suitable type and may be configured to carry out any suitable nucleic acid amplification technique, such as LAMP or PCR. Although described in the context of the systems of FIG. 1, the example technique of FIG. 5B may be carried out using any suitable nucleic acid amplification device and computing device. More specific aspects and examples of the technique generally illustrated in FIG. 5B are described below with respect to 10A-10C.

In the example approach of FIG. 5B, nucleic acid amplification device 8 amplifies a target nucleic acid within an enriched sample within reaction chamber 10 and detector 16 obtains a data set including measurements representative of (80). In some examples, the sample may be derived from food production environment 60, raw material 62, or end product 66 as described above with respect to FIG. 4. Nucleic acid extracted from the sample may be placed within a reaction vessel (e.g., a PCR tube) along with a light-emitting species that emits light in a stoichiometric relationship with the target nucleic acid, which may be a DNA sequence associated with a target organism (e.g., a bacterial genus or species). In some examples, the sample may be an enriched sample derived from a sample of food or feed raw material, end product, water or production environment. For example, the sample placed in the reaction vessel may be an enriched sample from a culture derived from the initial sample.

Detector 16 of nucleic acid amplification device 8 captures a data set comprising time-series measurement samples of the light emitted by the light-emitting species over one or more amplification cycles and transmits the data set to computing device 42 of user device 20, a computing device of access point 24, or any other suitable computing device (82). In some examples, the data set may correspond to a particular portion or phase of the amplification cycle, such an initial portion or phase occurring at the beginning of the amplification cycle and a subsequent phase. In some example nucleic acid amplification techniques (e.g., a LAMP technique), a light-emitting species, such as luciferin, may emit light as nucleic acid detection deice 8 heats to a temperature at which the amplification cycle is carried out.

In the example of user device 20, one or more of processors 23, signal processing module 52, and/or other components of computing device 42 may apply a trained machine learning system to the data set to determine whether the biological assay tested negative for the target nucleic acid due to matrix inhibition but would have tested positive for the target nucleic acid had matrix inhibition not been present (84) or a true negative. In some examples, the data set may be associated with a background or baseline signal occurring during a first portion of the biological assay (e.g., within about the first five minutes of the biological assay), as further described below with respect to FIGS. 8, 9, and others. It should be noted that what is described is inhibition based on inhibitory materials in a sample. The techniques described may be applied to other forms of inhibition, and to other reasons for misclassification of samples in nucleic acid amplification assays.

Figure 6:
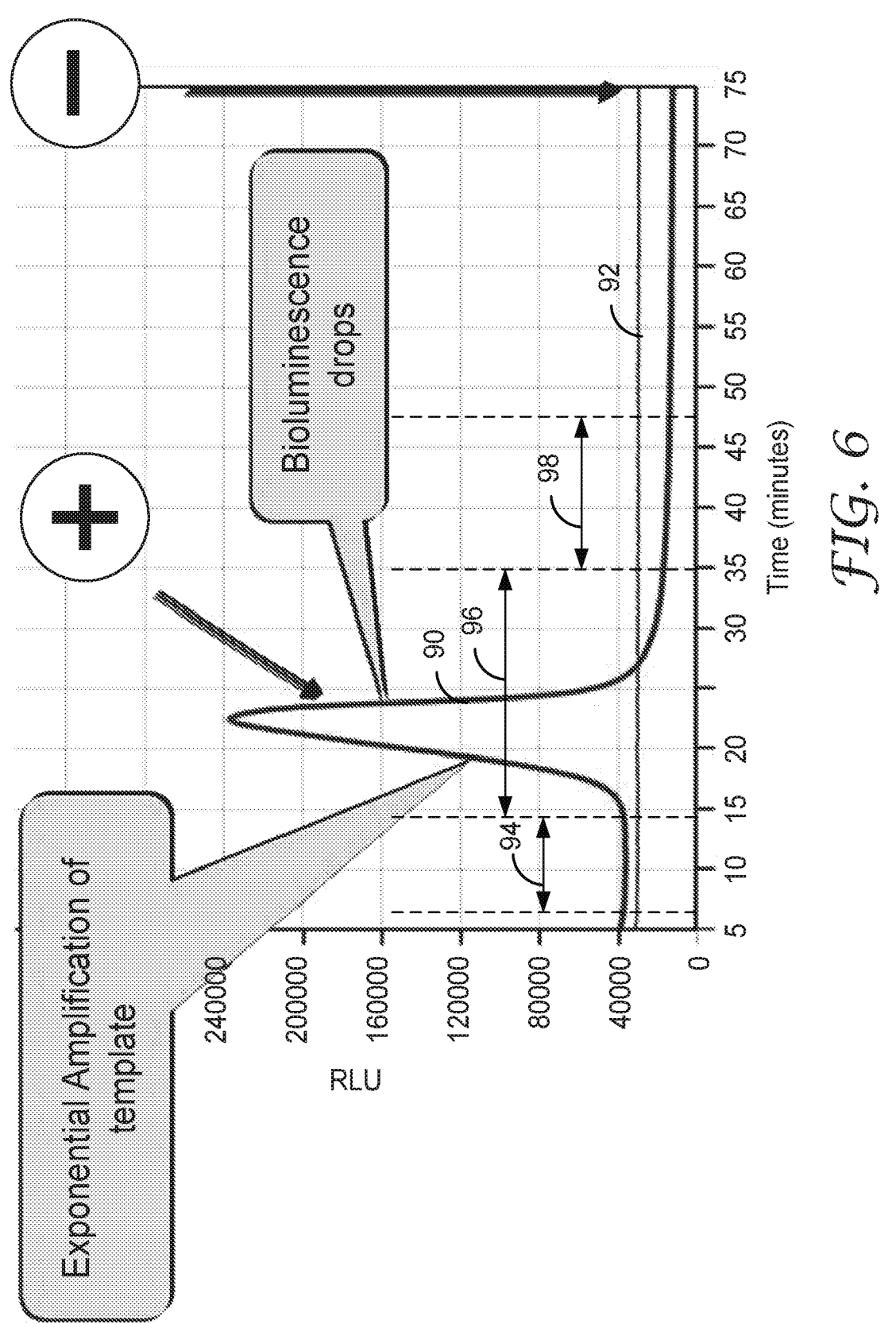
FIG. 6 illustrates real-time detection of nucleic acid amplification during a LAMP amplification cycle based on measurements of bioluminescence intensity over time, in accordance with one aspect of this disclosure.
Figure 7:
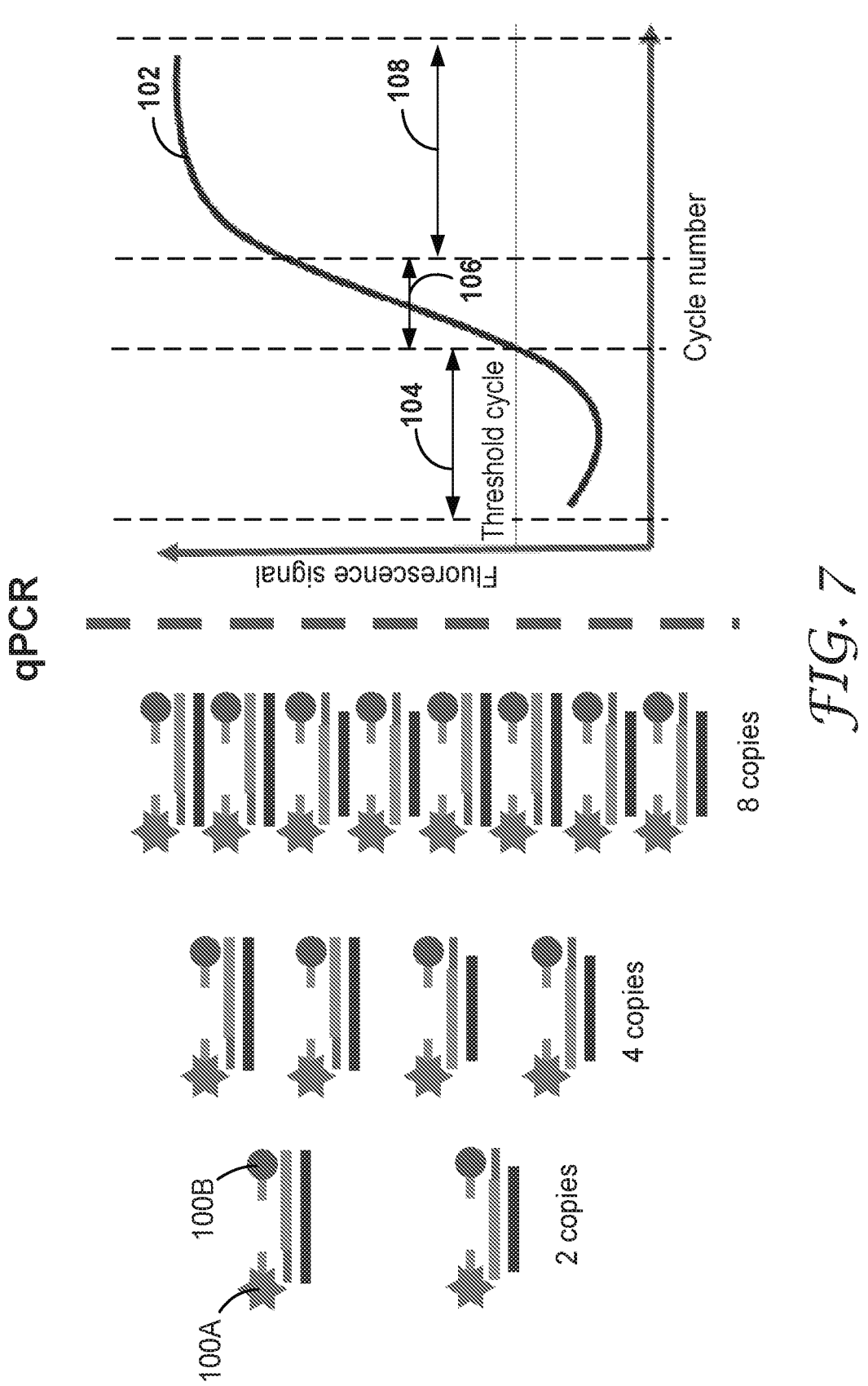
FIG. 7 is a schematic drawing illustrating representative features of an example qPCR technique, in accordance with one aspect of this disclosure.

FIGS. 6 and 7 are conceptual drawings illustrating representative features of example nucleic acid amplification techniques that may be used with the systems and methods described herein. Technical aspects of an example LAMP technique are described below with respect to FIG. 6, such as to the extent that such technical aspects may be relevant to arriving at the example of FIG. 6. FIG. 7 illustrates aspects of an example qPCR technique that may be used with the systems and methods described herein. Technical aspects of an example qPCR technique are discussed below with respect to FIG. 7, such as to an extent that such technical aspects may be relevant to arriving at the example of FIG. 7. However, it should be understood that the systems and methods described herein may be used with any suitable nucleic acid amplification technique, and are not limited to the particular examples described with respect to FIGS. 6 and 7.

LAMP uses strand-displacing Bst DNA polymerase and four to six primers to produce continuous DNA amplification at a constant temperature (i.e., under isothermal conditions). In LAMP techniques, amplification and detection of a target nucleic acid can be completed in a single step, by incubating a mixture of a sample, primers, a DNA polymerase with strand displacement activity, and substrates at a constant temperature (about 65° C.). In some examples, LAMP may provide high amplification efficiency, with DNA being amplified $10^9$-$10^{10}$ times in 15-60 minutes. Because of its high specificity, the presence of amplified product can indicate the presence of target gene.

In LAMP, four different primers recognize six distinct regions in a template (i.e., target) DNA sequence and two loop primers recognize two additional sites in corresponding single stranded loop regions during LAMP. The four different primers that recognize the six distinct regions of the target DNA may include a Forward Internal Primer (FIP), a Forward Outer Primer (F3; aka FOP), a Backward Inner Primer (BIP), and a Backward Outer Primer (B3; aka BOP). The two loop primers include Forward Loop Primer (FLP) and Backward Loop Primer (BLP). In contrast, PCR and qPCR each use non-strand displacing Taq DNA polymerase and two corresponding primers, a forward primer and a backward primer to recognize two distinct regions. In addition, qPCR uses a probe (e.g., a fluorescence-emitting molecular beacon probe, a fluorescence-emitting hydrolysis probe, a primer carrying a fluorescence-emitting probe element, or another suitable probe that includes a fluorescent moiety) having specificity to a third distinct region.

The two loop primers FL and BL may bind to additional sites during LAMP and accelerate reactions. For example, primers containing sequences complementary to the single stranded loop region (either between the B1 and B2 regions, or between the F1 and F2 regions) on the 5' end of a dumbbell-like structure formed during LAMP may provide an increased number of starting points for DNA synthesis during a LAMP technique. For example, an amplified product containing six loops (not shown) may be formed during LAMP. In example techniques in which loop primers FL and BL are not used, four out of six of such loops would not be used. Through the use of loop primers, all the single stranded loops can be used as starting points for DNA synthesis, thereby reducing amplification time. For example, the time required for amplification with loop primers may be about one-third to about one-half of the time required for amplification in examples in which loop primers are not used. In some examples, with the use of loop primers, amplification may be achieved within 30 minutes.

FIG. 6 illustrates real-time detection of nucleic acid amplification during a LAMP amplification cycle based on measurements of bioluminescence intensity over time, in accordance with one aspect of this disclosure. In an example LAMP technique, isothermal DNA amplification releases pyrophosphate (PPi) as a byproduct. The byproduct PPi is then converted to adenosine triphosphate (ATP) by the enzyme ATP-sulfurylase in the presence of adenosine 5'-phosphosulfate. In one such example approach, a biological assay having a sample being analyzed for a target nucleic acid may be adapted to include the luciferase enzyme and its substrate luciferin, the latter of which may be used as the light-emitting species in the example systems and methods described herein. Since ATP is a co-factor for the reaction of the luciferase enzyme and bioluminescence-producing luciferin, the conversion of PPi to ATP during an amplification cycle of a LAMP technique drives the emission of bioluminescence. This emission of bioluminescence may be detected by a detector of a nucleic acid amplification device configured for LAMP, such as detector 16 of nucleic acid amplification device 8 of FIGS. 1 and 2, and data representing time-series measurements of the bioluminescence are stored as a data set. In some examples, the mechanism for generating light during a LAMP technique illustrated in FIG. 6 may provide one or more other benefits, such as enabling real-time detection of nucleic acid amplification occurring during the LAMP amplification cycle over a relatively short period of time, such as about 15 minutes.

Time-series measurements of relative light units (RLU) emitted by the light-emitting species (e.g., luciferin) in a biological assay containing the target nucleic acid are depicted in curve 90. Time-series measurements of relative light units (RLU) emitted by the light-emitting species (e.g., luciferin) in a control not containing the target nucleic acid are depicted in baseline curve 92. As shown by curve 90, exponential amplification of the target nucleic acid during the LAMP amplification cycle produces a bioluminescence signal having both a rapid increase in RLU and a rapid decrease in RLU. Portions of curve 90 prior to and/or after the peak may be associated with a background or baseline portion of the light signal and may be used in systems and methods described herein for training and using a machine-learning system to determine whether a sample is inhibited by a matrix. In some examples, the time-to-peak RLU emission corresponds to the quantity of the target organism. For example, a relatively greater quantity of the target organism may produce a shorter time-to-peak RLU emission. Thus, one or more aspects of curve 90, such as the time-to-peak or amplitude, may be used in training a machine learning system to estimate a quantity of a target organism in examples in which quantitating the target organism may be desirable.

In some examples, the data set used to train a machine learning system such as a system includes data captured as a set of time-series measurement samples of biolumines-cence captured across the entirety of the amplification cycle. In one such example, luminescence measurements are taken approximately every 5 seconds, which may be accumulated as measurements at 10, 15, 20, and/or 25 second intervals across the amplification cycle for reporting purposes.

In some example approaches, the data set used to train a machine learning system such as a system includes time-series measurement samples of bioluminescence taken across the entirety of the nucleic acid amplification cycle. In other example approaches, the training data set includes measurements taken during one or more of a first phase 94 of the amplification cycle, a second phase 96 of the ampli-fication cycle and a third phase 98 of the amplification cycle. In some such examples, a machine learning system may be trained to estimate a quantity of the target organism present in a sample based on samples in each of the first, second, and third data subsets, based on the data set of samples taken across the entire amplification cycle, or based just on samples in the second subset. In one such example approach, the samples from the second subset include a sample taken at $T_{max}$, where $T_{max}$ is the time during the nucleic acid amplification cycle that the maximum amplitude of the target nucleic acid is detected. Again, samples may be taken approximately every 5 seconds, which may be accumulated to measurements from about 10, 15, 20, and/or 25 seconds across the amplification cycle for reporting purposes. Train-ing the machine learning system based in part on data subsets not associated with peak amplification may provide more robust training than training based only on one or more data subsets associated with peak amplification, which in turn may enhance the ability of the trained machine learning system to accurately estimate an unknown quantity of the target organism in examples in which quantitating the target organism may be desirable.

A detector, such as detector 16 of nucleic acid amplifi-cation device 8, may capture a data set that includes time-series measurement samples of the light emitted by the light-emitting species during the amplification cycle as depicted in curve 90 and transmit the data set to a computing device (e.g., computing device 42). In some examples, the data set may include time-series measurement samples asso-ciated with portions of curve 90 prior to and/or after the peak may be associated with a background or baseline portion of the light signal and may be used in systems and methods described herein for training and using a machine-learning system to determine whether a sample is inhibited by a matrix. In this manner, the mechanism for generating light during a LAMP technique described with respect to FIG. 6 may enable a user to obtain an indication of whether a biological assay is inhibited with greater accuracy than may be achieved by diluting and re-analyzing the sample, as dilution may cause loss of signal associated with the target nucleic acid if the initial quantity of the nucleic acid preset in the sample was relatively low. This mechanism also may enable a user to obtain an estimated quantity of the target organism in the sample much sooner than may be practicable using traditional pathogen quantitation methods.

In PCR, DNA extension is limited to a specific period of each thermocycle (i.e., amplification cycle). In PCR, the presence of inhibitors can prevent the polymerase from extending the DNA in the time allowed, which may result in incomplete amplification products and may add to inhibition caused by an inhibitory matrix, thereby preventing the detection of the target organism. PCR's temperature cycling and the association and disassociation of the polymerase from the DNA template during the denaturation step pro-vides many opportunities for inhibitors to interfere. Inhibi-tion may be less likely to occur in LAMP techniques than in PCR- and Immunoassay-based systems. Also, PCR may be more likely to be subject to interference by the natural fluorescence of some food samples and enrichment media. Thus, use of LAMP techniques may provide one or more benefits over the use of PCR techniques in the systems and methods described herein. However, as discussed above, the use of PCR techniques in conjunction with the systems and methods described herein may provide one or more benefits over traditional pathogen detection and/or quantitation methods in other examples.

FIG. 7 illustrates detection of nucleic acid amplification during an example qPCR technique across multiple PCR cycles based on measurements of fluorescence intensity over time, in accordance with one aspect of this disclosure. In some such examples, a light-emitting species may be a fluorescence-emitting hydrolysis probe, such as a TaqMan hydrolysis probe (available from Thermo Fisher Scientific). During PCR, 5'-3' exonuclease activity of the Taq poly-merase cleaves the probe into two portions, 100A and 100B, during hybridization to a complementary target DNA sequence. Cleavage of the hydrolysis probe produces a fluorescence signal, represented in FIG. 7 by curve 102.

As shown by curve 102, amplification of the target nucleic acid during the PCR run including multiple amplification cycles produces a fluorescence signal. Curve 102 may include several portions or phases that reflect corresponding portions or phases of amplification of the target nucleic acid. For example, curve 102 may include a first portion corre-sponding to an initiation phase of amplification, during which the fluorescence signal may remain below a thresh-old. Curve 102 further may include a second portion corre-sponding to an exponential phase of amplification, during which the fluorescence exceeds the threshold and increases exponentially. Finally, curve 102 may include a third portion corresponding to a plateau phase of amplification, during which the fluorescence remains above threshold and slowly increases over additional amplification cycles. Similar to the example LAMP technique of FIG. 6, portions of curve 102 prior to and/or after the exponential phase may be associated with a background or baseline portion of the light signal and may be used in systems and methods described herein for training and using a machine-learning system to detect matrix inhibition of a biological assay.

In addition, and as with the example LAMP technique of FIG. 6, a machine learning system may be trained to estimate a quantity of the target organism present in a sample based on each of the first, second, and third data subsets corresponding to respective ones of the first, second, and third phases of the fluorescence signal as noted above. The machine learning system may also be trained to estimate a quantity of the target organism present in the sample based on a data set of fluorescence signal measurements collected across the entirety of the amplification cycle. Training the machine learning system based in part on data subsets not associated with the exponential amplification phase of a PCR run (e.g., background fluorescence generated at the start of the amplification cycle) may provide more robust training than training based only on one or more data subsets associated with peak amplification (e.g., at least a subset containing the exponential phase), which in turn may enhance the ability of the trained machine learning system to accurately estimate an unknown quantity of the target organism.

Figure 8A:
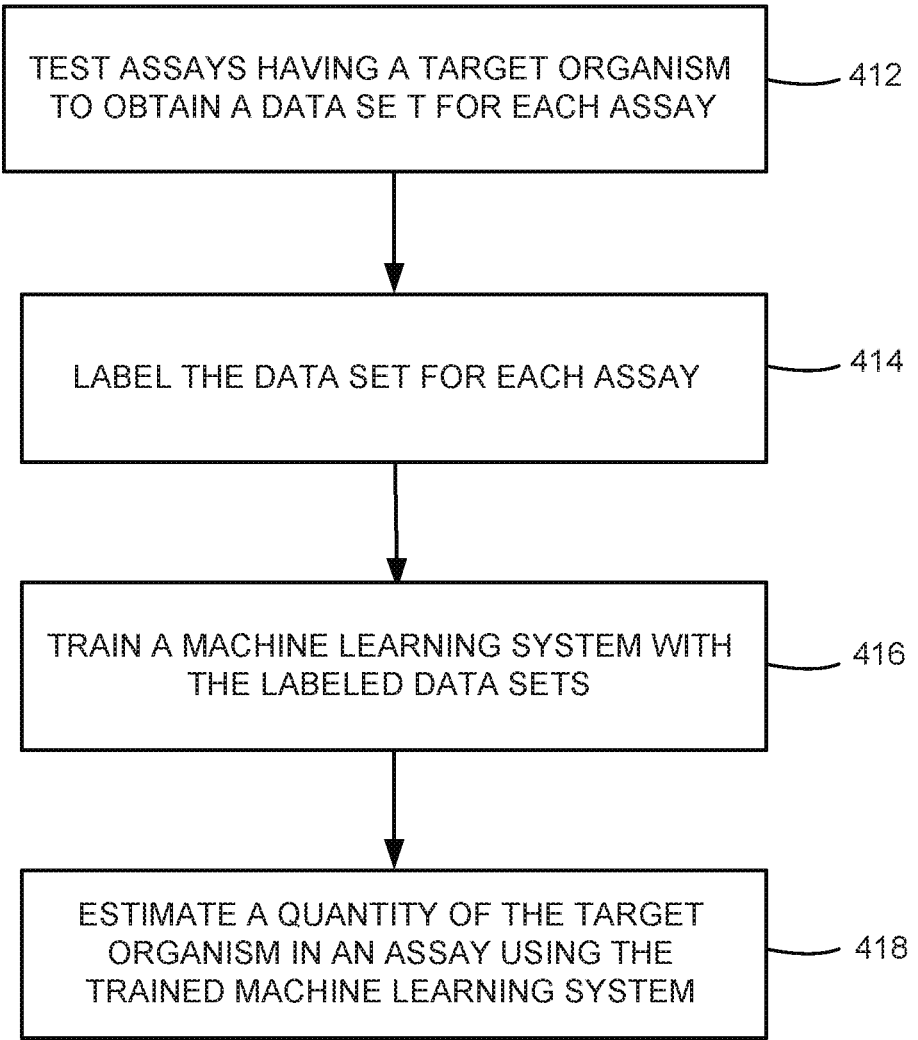
FIG. 8A is a flow diagram illustrating an example approach for training a machine learning system, in accordance with aspects of this disclosure.

FIG. 8A is a flow diagram illustrating an example approach for training a machine learning system, in accordance with aspects of this disclosure. In the example approach of FIG. 8A, a nucleic acid amplification device 8 such as shown in FIG. 1 or FIG. 2 is used to test assays having cell concentrations of a target organism to obtain a data set for each assay (412). The assays may be from cultures, from matrices (including inhibitory matrices), or from both. Each data set is then labeled with a quantity reflective of the quantity of target organisms detected in each respective array by the nucleic acid amplification device (414). System 6 then trains a machine learning system using the labeled data sets (416) to estimate a quantity of the target organism in an assay. In some example approaches, the method further includes estimating a quantity of the target organism in an assay using the trained machine learning system (418). In some example approaches, the quantity of target organism associated with each assay is based on a priori knowledge of the sample (e.g., from a sample having a known cell concentration). Each data set is therefore labeled based on the a priori knowledge. In other example approaches, the quantity associated with each assay is based on quantitative testing of the sample, such as through the use of an alternative quantitation method such as, for example, MPN, and each data set is labeled based on the results provided by the alternative quantitative method.

In some example approaches, quantification of DNA-based assays is performed using high quality DNA and a single response value from a DNA amplification reporter. This response value, usually fluorescence or biolumines-cence, may be based on the signal surpassing a preset threshold value or on a peak amplitude value. In some examples, it may be desirable to estimate an initial quantity of more than one strain or species (e.g., within a genus) of a target organism in a sample, as more than one of such strains or species may be pathogenic.

In one example approach, culture preparation included inoculating 10 mL of Buffered Peptone Water (BPW, 3M Company, St. Paul) with a single colony from an agar plate corresponding to each strain (Table 1). The inoculated broths were incubated at 37° C. for 18 h.

TABLE 1

| Strain | Reference[1] |
| --- | --- |
| *Salmonella enterica* subsp. *enterica* serovar Typhimurium | ATCC ® 14028 ™ |
| *Salmonella enterica* subsp. *enterica* serovar Enteritidis | ATCC ® 13076 ™ |

TABLE 1-continued

| Strain | Reference[1] |
| --- | --- |
| *Salmonella enterica* subsp. *enterica* serovar Hadar | TC 164 |
| *Salmonella enterica* subsp. *enterica* serovar Infantis | ATCC ® 51741 ™ |
| *Salmonella enterica* subsp. *enterica* serovar Kentucky | TC 251 |

[1]American Type Culture Collection and Tecra ™ Collection.

For enumeration, the cultures were serially diluted in But-terfields Buffer and plated onto 3M™ brand Petrifilm™ Aerobic Count (AC) Plates (3M Company) (hereinafter "Petrifilm AC plates") following manufacturer's instruc-tions. The cultures were kept at 4-8° C. until plate count results were obtained. The counts obtained were used to estimate the number of cells used for the detection using 3M™ brand Molecular Detection Assay 2—*Salmonella* (3M Company) (hereinafter "MDA2—Sal"). A final plate count was conducted using Petrifilm AC plates at the time of conducting the detection assay. These final plate counts were used for reporting the concentration of cells.

In one example approach, each strain was serially diluted in Butterfield's Buffer to approximately $10^2$, $10^3$, $10^4$, $10^5$ and $10^6$ colony forming units (CFU) per milliliter. Aliquots from each dilution were analyzed using MDA2—Sal fol-lowing manufacturer's instructions. MDS software supplied by 3M Company was then used to determine the time-to-peak, a response to the amplification of the target sequence. A dataset of time-to-peak for known concentrations of cells was then used to train a Decision Forest Regression model and a Boosted Decision Tree model. Both approaches yielded coefficients of determination of approximately 0.75. The same dataset used to train a linear regression model yielded a coefficient of determination $R^2$ of approximately 0.2912. Other regression techniques, such as support vector regression, random forest regression, ridge regression, logis-tic regression, Lasso, and nearest neighbor regression, may also be used to train models based on data sets of time-to-peak for known concentrations of cells.

Time-to-peak response is not always the best measure of cell count. Differing matrices (i.e., substances other than a pure culture in a sample or molecular components in food sample) may prevent good agreement between time-to-peak response and actual cell counts. A count of cells of a *Salmonella* strain may, for instance, produce different time-to-peak measurements depending on the matrix in which the cells are located. For example, different time-to-peak mea-surements may result from a particular count of cells of the *Salmonella* strain in a salmon matrix versus a shellfish matrix, or in other such matrices. In some example approaches, measurements of parameters such as light inten-sity over time across a nucleic acid amplification cycle provide a better representation of initial cell count. Even then, it may be advantageous to train a machine learning system with different matrices to more accurately estimate quantity of a target organism within a particular matrix.

In some example approaches, each data set includes time-series measurement samples of the light intensity detected by detector 16 during an amplification cycle. Each data set is labeled with known cell concentration of its respective assay and the labeled data set is then used to train a machine learning system 25 or 35 as detailed below. Machine learning system 25 or 35 is then used to estimate a quantity of the target organism in each assay. In some example approaches, a different data set is used for each matrix or type of matrix. A matrix representing target organisms in cheese may be used, for example, to train a machine learning system 25 or 35 for use in quantitating target organisms in a cheese factory.

In some example approaches, each data set includes light intensity measurements made over time during one or more amplification cycles. In some such example approaches, each data set includes the time-series measurements of light intensity captured across the whole of the amplification cycle. In some example approaches, such data sets also include measurements made during a period at the start of the amplification cycle where the data is typically either not captured, discarded or otherwise suppressed by nucleic acid amplification device 8. In some example approaches, each data set includes light intensity measurements made in a first period before $T_{max}$, light intensity measurements made in a second period of time including $T_{max}$, and light intensity measurements made in a third period of time occurring after $T_{max}$.

Figure 8B:
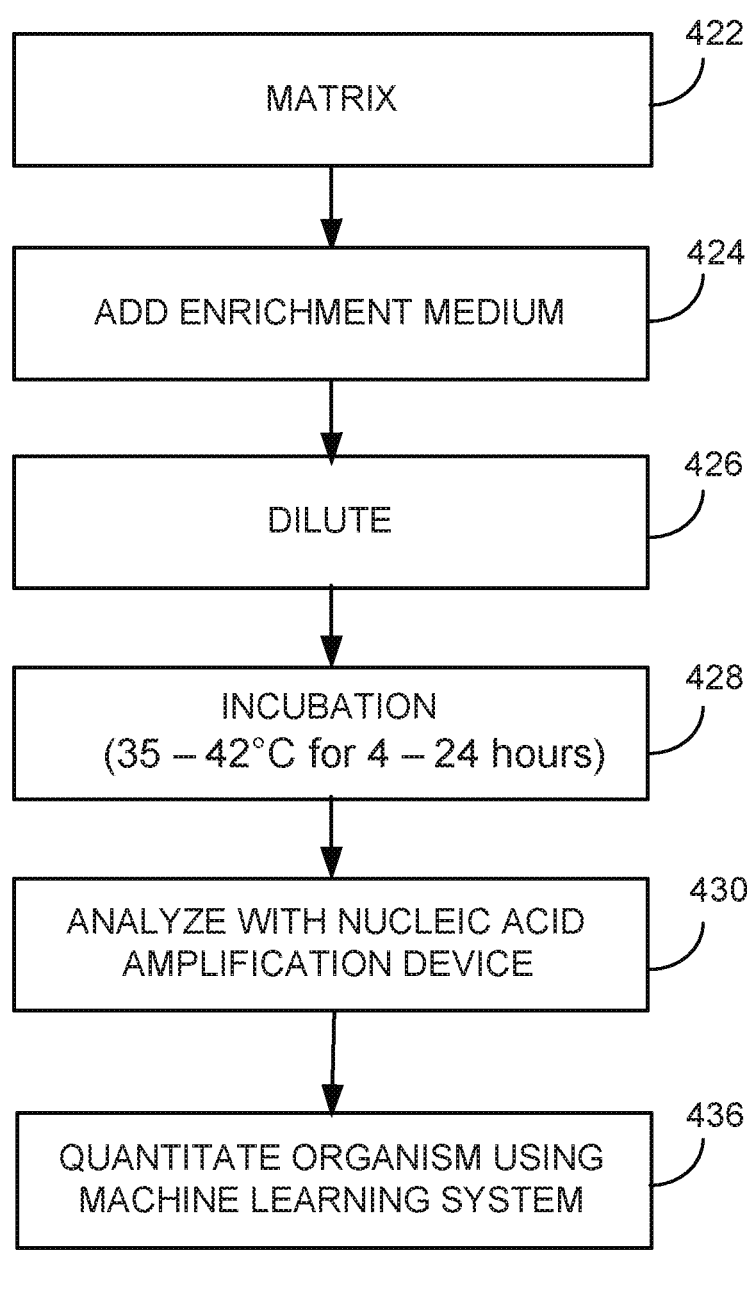
FIG. 8B is a flow diagram illustrating an example approach that uses the trained machine learning system of FIG. 8A to estimate a quantity of a target organism, in accordance with aspects of this disclosure.

FIG. 8B is a flow diagram illustrating an example approach that uses the trained machine learning system of FIG. 8A to estimate a quantity of a target organism, in accordance with aspects of this disclosure. In the example approach of FIG. 8B, the method includes receiving a sample of a matrix (422), such as by a laboratory worker or automated equipment. The matrix may be, for example, a matrix in which the target organism may be found, such as the poultry rinse matrix, or a portion of a raw material of a food product or end product of a food product. Upon receiving the matrix, the laboratory worker or equipment adds an appropriate enrichment medium configured to enable growth of the target organism within the sample containing the target organism and the matrix to a detectable limit (424). In some examples, such as examples in which a PCR technique is used for amplification of target nucleic acid, an appropriate enrichment medium may have a characteristic of being less likely to interfere with the fluorescence emitted during PCR than one or more otherwise appropriate enrichment media, such as by emitting less background fluorescence relative to other appropriate media. Next, in some example approaches, the worker or equipment prepares a 1:10 dilution of the resulting enrichment solution (426). The use of a 1:10 dilution may increase the specificity of the trained machine learning system for the target organism. Other suitable dilutions may be used, such as 1:100 or 1:1000. The amount of dilution will, in some example approaches, depend on system characteristics such as the type of organism targeted and the particular amplification technique.

Next, the sample within the enrichment solution is incubated to allow enrichment of the target organism (428). In some examples, the sample may be incubated at about 35-42° C. for about 4-24 hours, or at any other suitable temperature and period of time that may enable suitable growth of the target organism. In other examples, an enrichment step may not be used, but instead the nucleic acid may be extracted from a sample without enrichment. Following incubation, if used, the sample is analyzed via, in some example approaches, amplification and detection of the target nucleic acid associated with the target organism (430). For example, the target nucleic acid may be amplified and detected using a nucleic acid amplification device 8 having a light detector 16 such as a Molecular Detection System (MDS) available from 3M Company of St. Paul, Minn. The MDS, for example, may be configured to amplify the target nucleic acid by carrying out a LAMP technique and may then detect bioluminescence emitted by a light-emitting species within the sample (e.g., luciferin) using detector 16. By combining LAMP with bioluminescence detection, nucleic acid amplification devices such as the MDS may make molecular detection of foodborne pathogens simpler and faster, thereby providing users with speed and ease in simultaneously identifying one or more target organisms (e.g., one or more species or strains of Salmonella, Listeria, Listeria monocytogenes, E. coli O157 (including H7), Campylobacter, Cronobacter and/or other target organisms) in food and/or environmental samples. In other example approaches, the techniques of FIGS. 8A and 8B are carried out using a different LAMP platform or using a PCR platform or a different nucleic acid amplification platform.

In some example approaches, the amplitude of light generated early in an amplification cycle (e.g., before phase 94 or phase 104) may be suppressed (e.g., not recorded) so as to not confuse users with background activity. It has been found, however, that such information may be helpful in training the machine learning system. Therefore, in one example approach, the data set includes time-series measurements made before phase 94 in FIG. 6. In a similar example approach, the data set includes time-series measurements made before phase 104 in FIG. 7.

In some example approaches, labeled data sets are produced by expert inspection of individual samples on which nucleic acid amplification has been performed. In one such example approach, an expert receives data sets associated with the samples, determines a quantity of organisms and/or target nucleic acid in the sample (via, for example, one of the traditional quantification techniques described above such as MPN) and labels each data set with the determined quantity value. The labeled data sets are then used to train a machine learning system, as depicted in FIG. 8A.

In some example approaches, data sets include time-series measurements taken at predetermined intervals (e.g., 25 seconds) across the whole of the amplification cycle. In other example approaches, data sets include data selected from certain phases of the amplification cycle. For instance, a data set may include data from one or more of phases 94, 96 and 98 in FIG. 6 or from one or more of phases 104, 106 and 108 in FIG. 7. For example, where (430) includes a LAMP technique, the data set may include one or more data subsets as described with respect to FIG. 6. For example, the data set may include a first data subset representing time-series measurement samples of light emitted up to a first point in time in the amplification cycle, the first point in time occurring prior to a peak amplitude of the light emitted over the amplification cycle, a second data subset representing time-series measurement samples of light emitted after the first point in time but before a second point in time in the amplification cycle, the second point in time occurring after the peak amplitude, and a third data subset representing time-series measurement samples of light emitted after the second point in time in the amplification cycle. A computing device (e.g., processing circuitry 30 of external device 28 of FIG. 2 or any other suitable computing device) then trains a machine learning system to predict the initial concentration (i.e., quantity) of the target organism of interest (see FIG. 8A).

In one example, the computing device may label a data set, and/or one or more subsets of the data set, with an estimate of the quantity of the target organism within the biological assay associated with the respective data set or data subset. The computing device then trains the machine learning system with the labeled data sets (or data subsets) and/or matrix identity to estimate a quantity of the target organism within the sample, resulting in a trained model. The computing device then may store the parameters of the trained machine learning system to one or more storage components of a system, such as a memory of a computing device, user device 20, a memory of a computing device of access point 24, and/or to any other suitable location.

In a workflow technique associated with using a trained machine learning system to calculate a quantity of the organism of interest, the technique of FIG. 8B includes carrying out steps 422-436 in substantially the same way as when data sets were collected to train the machine learning system. The matrix at (422) may be a sample of a raw food material, an end food product, or an environmental sample that may contain a target organism of interest instead of a known quantity of the target organism. In such examples, a nucleic acid amplification and detection system, such as the MDS or another system configured to carry out LAMP or PCR and detect light emitted by light-emitting species during one or more amplification cycles, may capture a data set, the data set comprising time-series measurement samples of the light emitted by the light-emitting species during the amplification cycle and analyze the data set (430). The data set is then analyzed based on the trained machine learning model to arrive at an estimate of the quantity of the target organism in the matrix (436).

In some such examples the data set may include one or more data subsets corresponding to one or more portions of an amplification cycle, such as in a manner similar to data subsets with which the machine learning system is trained. For example, a data set corresponding to a sample containing an unknown quantity of a target organism may include a first data subset representing time-series measurement samples of light emitted up to a first point in time in the amplification cycle, the first point in time occurring prior to a peak amplitude of the light emitted over the amplification cycle, a second data subset representing time-series measurement samples of light emitted after the first point in time but before a second point in time in the amplification cycle, the second point in time occurring after the peak amplitude, and a third data subset representing time-series measurement samples of light emitted after the second point in time in the amplification cycle. A computing device configured to receive the first, second, and third data subsets (e.g., computing device 42 of user device 20, a computing device of access point 24, or any other suitable computing device) applies the trained machine learning system to the data subsets (436) and calculates the concentration (e.g., quantity) of the target organism of interest in the sample. In some examples, the computing device then may store one or more such estimated quantities to one or more storage components of a system, such as a memory of an MDS, a memory of a computing device user device 20, a memory of a computing device of access point 24, and/or to any other suitable location.

In some example approaches, separate machine learning systems are trained as a function of the type of matrix being tested. For instance, a separate system may be trained for testing cheese, or for testing feed, with the parameters of each machine language machine learning system stored in memory based on the type of matrix being tested.

Figure 9:
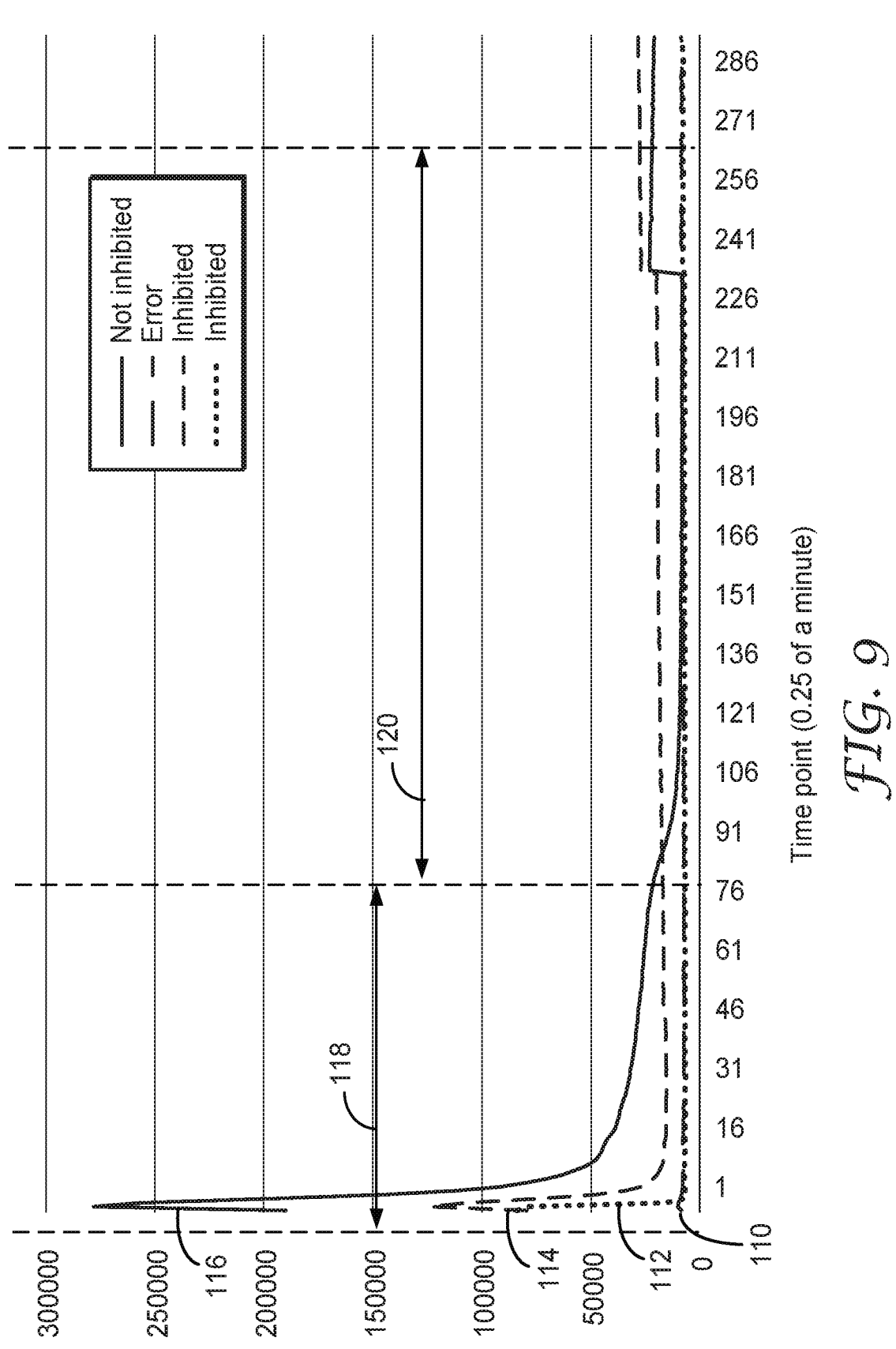
FIG. 9 illustrates a test results from an example pathogen detection system indicative of an assay error, an inhibited but valid assay, and a valid assay, in accordance with one aspect of this disclosure.

As noted above, it can be critical to reduce or eliminate false negatives while testing for the presence of target organisms in a sample. FIG. 9 illustrates test results from an example pathogen detection system indicative of a biological assay error 110, an inhibited and invalid biological assay 112, an inhibited but valid biological assay 114, and a valid and uninhibited biological assay 116, in accordance with one aspect of this disclosure. Some nucleic acid amplification and detection systems are configured to analyze a background or baseline signal (in RLU) the first five minutes of the biological assay. During this time, a peak in RLU is detected as part of the biochemistry engineered in the reaction and the biological assay is considered acceptable for analysis. If the peak is absent, an error message may be reported to the user. However, a matrix can be inhibitory to the biological assay and still produce a valid signal and a false negative result might be reported to the user, as in the example of inhibited but valid biological assay 114. Additional challenges may be present with matrices that generate a high baseline signal, such as matrices containing high concentrations of inorganic phosphorus, and those that will generate a low baseline, such as dark or turbid matrices. In both such cases, the initial peak height or an average or otherwise statistically combined value alone are not reliable indicators of a valid or inhibited biological assay (i.e. a high or low background can yield a true negative (or positive) or a false negative result).

The reporting signal (here, the light emitted by the light-emitting species at the initial portion of the amplification cycle) may appear as a spike or peak in the output curve, as illustrated in FIG. 9 and further as discussed below with respect thereto. Such a spike or peak may be considered part of the background or baseline of the signal representative of the light within the sample during the amplification cycle, as the light corresponding to such an initial spike or peak is not necessarily associated with amplification of the target nucleic acid. The initial spike or peak in the output curve may be indicative of the validity of the biological assay but not necessarily indicative of whether the biological assay is inhibited. For example, the spike or peak in the output curve at the initial portion of the amplification cycle may not occur, which may indicate that the biological assay is invalid or inhibited. However, an initial spike or peak in the output curve may occur even in inhibited biological assays, although in such examples, the spike may not be large enough (e.g., have insufficient width and/or amplitude) to be indicative of a non-inhibited biological assay.

Thus, the presence or absence of an initial spike may not be a sufficient criterion for detecting inhibition of a biological assay. Moreover, a subsequent background or baseline value of the output curve may not be a sufficient criterion on which inhibition of a biological assay may be determined. Thus, in some examples, a data set used to train a machine-learning system or used by a trained machine-learning system may correspond to an initial portion or phase occurring at the beginning of the amplification cycle and a subsequent phase occurring after the initial spike or peak.

Figure 10A:
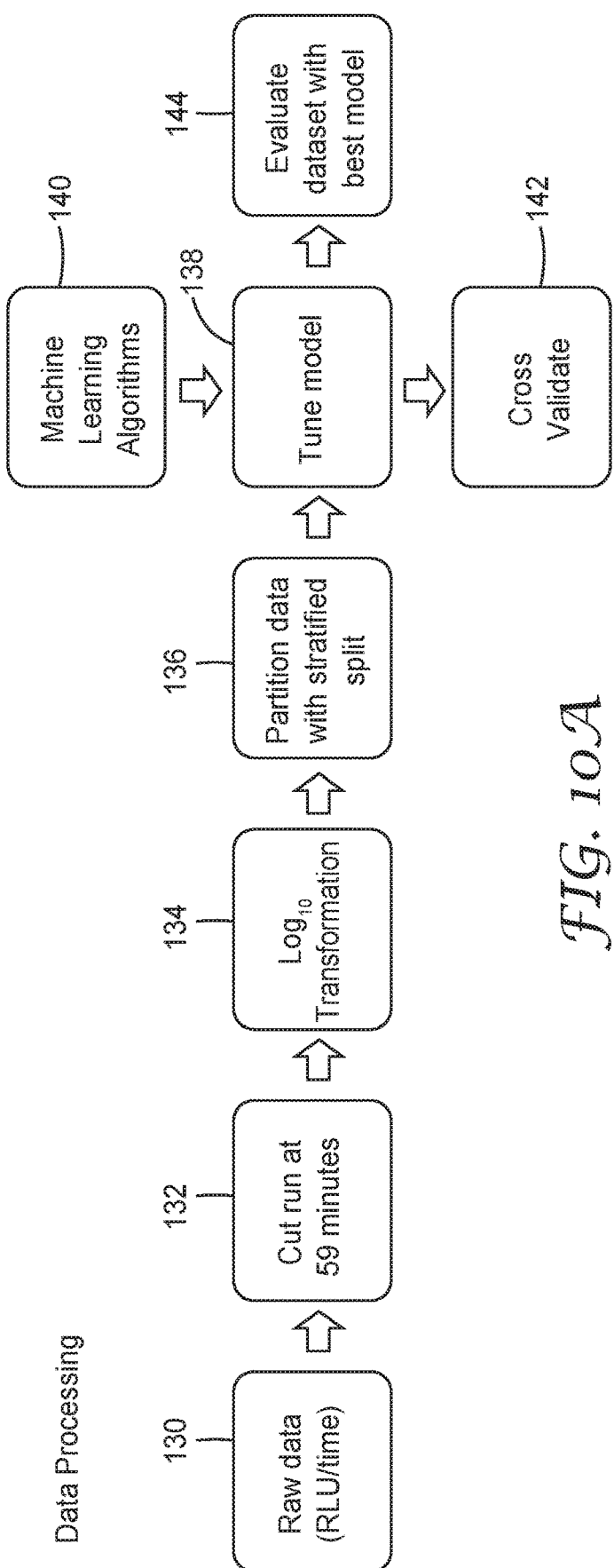
FIGS. 10A and 10B are flow diagrams illustrating example techniques for using data sets that tested negative for a target organism to train a machine-learning system to detect inhibited biological assays.
Figure 10B:
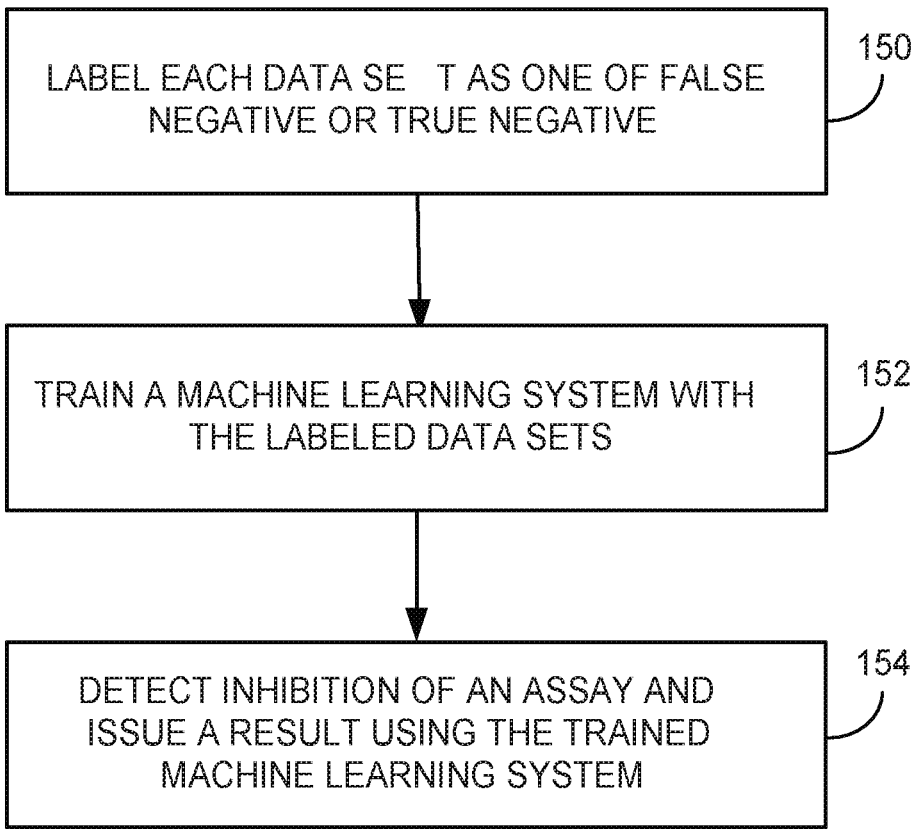

FIGS. 10A and 10B are flow diagrams illustrating example techniques for using data sets that tested negative for a target organism to train a machine-learning system to detect inhibited biological assays. In other example approaches, the data sets capture time-to-peak measurements of each assay. In some example approaches, provide time-series measurements of reporter signal intensity across some or substantially all of the amplification cycle. In yet other example approaches, the data sets provide time-series measurements of reporter signal intensity across portions of two or more amplification cycles. In yet other example approaches, the data sets provide time-series measurements of reporter signal intensity across substantially all of two or more amplification cycles. In some example approaches, the data sets include data associated with background or baseline signals captured by the nucleic acid amplification device.

In some example approaches of FIGS. 10A and 10B, labeled data sets are produced by expert inspection of individual samples on which nucleic acid amplification has been performed. In one such example approach, an expert receives data sets associated with samples that tested negative for the target organism, determines whether the sample is a false negative and labels each data set as true negative or false negative accordingly. The labeled data sets are then used to train a machine learning system, as depicted in FIGS. 10A and 10B.

In the example flowchart of FIG. 10A, data sets from assays that tested negative for the target organism were used to train a machine-learning system to detect inhibited biological assays. In one example approach, the machine-learning system was trained to estimate the probability that a background signal of a biological assay corresponds to a matrix-inhibited biological assay (i.e., rendering the biological assay unable to produce a positive reaction). In one example approach, the plurality of data sets included 2,186 separate data sets, each data set including analyses of raw data (RLU over time). In one example approach, the plurality of data sets were taken from 22 different manufacturing lots, and included 701 inhibited (false negative) samples and 1,485 true negative samples.

Generally, the data sets used to train a machine-learning system to detect false negatives come from biological assays that have tested negative for the target nucleic acid. As noted above, such negative results may include both truly negative results and false negative results. The false negative results may, in some instances, be associated with biological assays that tested negative for the target nucleic acid due to matrix inhibition and that would have tested positive had matrix inhibition not been present.

A representative data set will be discussed next. In some example approaches, device 8 captures data indicative of a reporting signal as raw data (RLU over time) time-series measurements of the reporting signal. In one LAMP-related approach, the raw data represents measurements, by a detector, of light emitted within the respective biological assay during an amplification cycle performed by a nucleic acid amplification device on the respective biological assay.

In one example approach, the raw data is received as a data set (130). In some example approaches, data sets from different sources are trimmed to a common run time (such as 59 minutes) (132). The data sets are log10 transformed (134). In one example approach, the data sets of the plurality of data sets are randomly partitioned with a stratified split to ensure that a representative number of inhibited (i.e., false negative) samples are present in each partition, as they may be underrepresented in a plurality of data sets (136). A training platform, such as a Microsoft Azure™ platform is then used to train one or more machine-learning systems using the optimal parameters found by a tuning model (138). However, it should be understood that any suitable training platform may be used in carrying out methods for training a machine-learning system as described herein in other examples.

In some examples, training a machine-learning system may include labeling, as false negative data sets, those data sets from the plurality of data sets that are associated with biological assays that tested negative for the target nucleic acid due to matrix inhibition and that would have tested positive had matrix inhibition not been present, and labeling, as true negative data sets, those data sets from the plurality of data sets that are associated with biological assays that tested negative for the target nucleic acid and that were not inhibited, such that training the machine-learning system with the true and false negative data sets enables the machine-learning system distinguish between biological assays of the target nucleic acid that truly test negative for the target nucleic acid and biological assays of the target nucleic acid that falsely test negative for the target nucleic acid due to matrix inhibition (140).

In the example of FIG. 10A, the trained models were cross validated by partitioning the data set in 10 slices that are individually used as validation set while the other nine are used to train the model (142). The average of the performance of the 10 partitions is presented for various models in Table 2 below. Finally, the plurality of data sets may be evaluated with the best-performing model to test the training methods, one or more of which may be stored to algorithm storage (described below with respect to FIG. 11) and/or to a user device (144). It should be understood that aspects of the plurality of data sets used in iteration of the example technique of FIG. 10A described above are illustrative in nature and should not be considered limiting to the technique of FIG. 10A. Any suitable plurality of data sets including inhibited (false negative) and true negative data sets from any suitable sources may be used in the technique of FIG. 10A. Additionally, or alternatively, one or more steps of the example technique of FIG. 10A may be optional (e.g., cutting run time (132) or others). In some examples, an example technique for training a machine-learning system may include one or more additional steps not illustrated in FIG. 10A.

TABLE 2

| | Target analyte of assays in the data set. | | | | | | |
|---|---|---|---|---|---|---|---|
| Model | True Positive | True Negative | False Positive | False Negative | Accuracy (%) | Precision (%) | Recall (%) |
| Two-class boosted decision tree | 1468 | 669 | 32 | 17 | 97.8 | 97.9 | 98.9 |
| Two-class decision forest | 1472 | 662 | 39 | 13 | 97.6 | 97.4 | 99.1 |
| Two-class regression | 1455 | 644 | 57 | 30 | 96 | 96.2 | 98 |
| Two-class locally deep support vector machine | 1457 | 664 | 37 | 28 | 96.2 | 97 | 97.4 |

In the example approach of FIG. 10B, a nucleic acid amplification device 8 in system 6 was used to test biological assays of samples. Data sets associated with samples that tested negative for a target organism are examined by an expert to determine if the test result was a true negative or a false negative, and each data set is labeled accordingly (150). Each data set may include measurements, performed on the associated biological assay by a nucleic acid amplification device of a specified type and collected over at least a portion of a nucleic acid amplification cycle, of the target nucleic acid detected within the associated biological assay and associated with a target organism. System 6 then trains a machine learning system using the labeled data sets (152). In some example approaches, the method further includes detecting inhibited biological assays and issuing a result indicating whether the biological assay tested negative for the target nucleic acid due to matrix inhibition using the trained machine learning system (154).

Figure 10C:
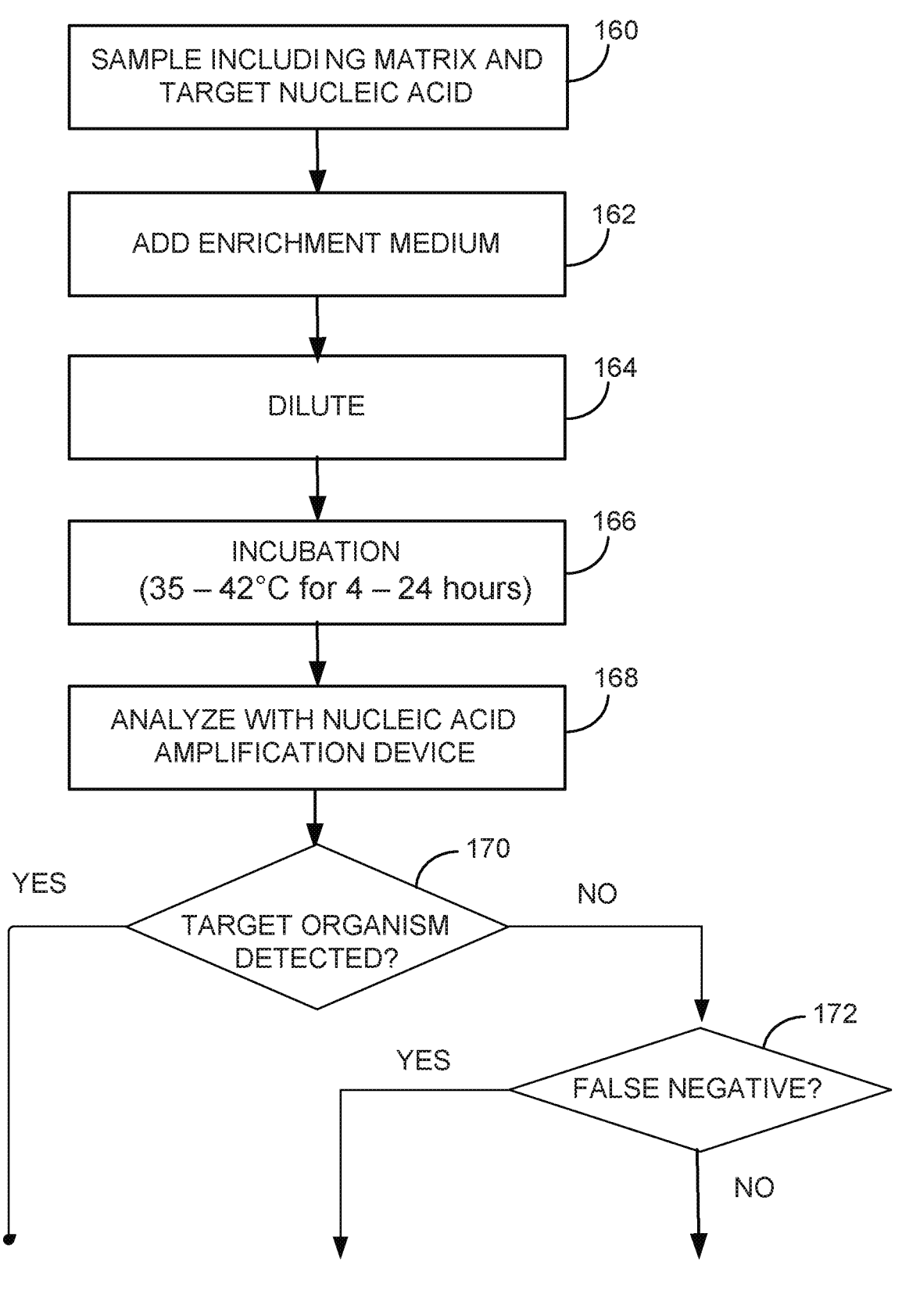
FIG. 10C is a flow diagram illustrating an example technique for using the trained machine learning system to detect inhibited biological assays, in accordance with one aspect of this disclosure.

FIG. 10C is a flow diagram illustrating an example technique for using the trained machine learning system to detect inhibited biological assays, in accordance with one aspect of this disclosure. In one such example approach of using a machine learning system to detect inhibited biological assays and to issue a result indicating whether a biological assay tested negative for a target nucleic acid due to matrix inhibition, the technique of FIG. 10C includes receiving a sample including a matrix and a quantity of a target nucleic acid (160), such as by a laboratory worker or automated equipment. The matrix may be, for example, a matrix in which a target organism associated with the target nucleic acid may be found, such portion of a raw material of a food product or end product of a food product. Upon receiving the sample, the laboratory worker or equipment adds an appropriate enrichment medium configured to enable growth of the target organism within the sample containing the target organism and the matrix to a detectable limit (162). In some examples, such as examples in which a PCR technique is used for amplification of target nucleic acid, an appropriate enrichment medium may have a characteristic of being less likely to interfere with the fluorescence emitted during PCR than one or more otherwise appropriate enrichment media, such as by emitting less background fluorescence relative to other appropriate media, which may help enable an accurate detection of whether the biological assay is inhibited due to matrix inhibition. Next, in some example approaches, the worker or equipment prepares a 1:10 dilution of the resulting enrichment solution (164).

Next, the sample within the enrichment solution is incubated to allow enrichment of the target organism (166). In some examples, the sample may be incubated at about 35-42° C. for about 4-24 hours, or at any other suitable temperature and period of time that may enable suitable growth of the target organism. In other examples, an enrichment step may not be used, but instead the nucleic acid may be extracted from a sample without enrichment. Following incubation, if used, the sample is analyzed via, in some example approaches, amplification and detection of the target nucleic acid associated with the target organism (168). For example, the target nucleic acid may be amplified and detected using a nucleic acid amplification device 8 having a light detector 16 such as the MDS. The MDS, for example, may be configured to amplify the target nucleic acid by carrying out a LAMP technique and may then detect bioluminescence emitted by a light-emitting species within the sample (e.g., luciferin) using detector 16. Next, system 6 applies the machine learning system trained to detect inhibited biological assays and issue a result indicating whether the biological assay tested negative for the target nucleic acid due to matrix inhibition (i.e., produced a false negative result). By combining LAMP with bioluminescence detection, nucleic acid amplification devices such as the MDS may make molecular detection of foodborne pathogens via detection of inhibited biological assays and/or quantitation of a target organism simpler and faster, thereby providing users with speed and ease in simultaneously identifying one or more target organisms (e.g., one or more species or strains of *Salmonella, Listeria, Listeria monocytogenes, E. coli* O157 (including H7), *Campylobacter, Cronobacter* and/or other target organisms) in food and/or environmental samples. In other example approaches, the techniques of FIGS. 9 and 10A-10C are carried out using a different LAMP platform or using a PCR platform or a different nucleic acid amplification and detection platform.

In some example approaches, each data set includes light intensity measurements made over time during one or more amplification cycles. In some such example approaches, each data set includes the time-series measurements of light intensity captured across the whole of the amplification cycle. In some example approaches, such data sets also include measurements made during a period at the start of the amplification cycle where the data is typically either not captured, discarded or otherwise suppressed by nucleic acid amplification device 8. In some example approaches, each data set includes light intensity measurements made in a first period before $T_{max}$, light intensity measurements made in a second period of time including $T_{max}$, and light intensity measurements made in a third period of time occurring after $T_{max}$.

In some example approaches of FIG. 10C, data sets include time-series measurements taken at predetermined intervals (e.g., 25 seconds) across the whole of the amplification cycle. In other example approaches, data sets include data selected from certain phases of the amplification cycle. For instance, a data set may include data from one or more of phases 94, 96 and 98 in FIG. 6 or from one or more of phases 104, 106 and 108 in FIG. 7. For example, where (152) includes a LAMP technique, the data set may include one or more data subsets as described with respect to FIG. 6. For example, the data set may include a first data subset representing time-series measurement samples of light emitted up to a first point in time in the amplification cycle, the first point in time occurring prior to a peak amplitude of the light emitted over the amplification cycle, a second data subset representing time-series measurement samples of light emitted after the first point in time but before a second point in time in the amplification cycle, the second point in time occurring after the peak amplitude, and a third data subset representing time-series measurement samples of light emitted after the second point in time in the amplification cycle. A computing device (e.g., processing circuitry 30 of external device 28 of FIG. 2 or any other suitable computing device) then trains a machine learning system to predict the initial concentration (i.e., quantity) of the target organism of interest (154). For example, the computing device may label a data set, and/or one or more subsets of the data set, with an estimate of the quantity of the target organism within the biological assay associated with the respective data set or data subset. The computing device then trains the machine learning system with the labeled data sets (or data subsets) and/or matrix identity to estimate a quantity of the target organism within the sample, resulting in a trained model. The computing device then may store the parameters of the trained machine learning system to one or more storage components of a system, such as a memory of a computing device, user device 20, a memory of a computing device of access point 24, and/or to any other suitable location.

In a workflow technique associated with using a trained machine learning system to determine whether a negative results is a false negative, the technique of FIG. 10C includes carrying out steps 160-172 substantially as described above with respect to an example technique for training the machine learning system, although the matrix at (160) may be a sample of a raw food material, an end food product, or an environmental sample that may contain a target organism of interest instead of a known quantity of the target organism. In such examples, a nucleic acid amplification and detection system, such as the MDS or another system configured to carry out LAMP or PCR and to detect light emitted by light-emitting species during one or more amplification cycles, may capture a data set, the data set comprising time-series measurement samples of the light emitted by the light-emitting species during the amplification cycle and analyze the data set (168). The data set is then analyzed based on the trained machine learning model discussed in the context of FIGS. 8A and 8B above to arrive at either an estimate of the quantity of the target organism in the matrix, or an indication of whether a threshold amount of the target organism is present. If the sample tests negative for the target organism, a check is made at (172) to determine if the results is a false negative (by, for instance, applying the machine learning system trained at (138) of FIG. 10A). In one such example approach, false negatives are flagged and reported to a user via user device 20.

In some such examples, the data set may include one or more data subsets corresponding to one or more portions of an amplification cycle, such as in a manner similar to data subsets with which the machine learning system is trained. For example, a data set corresponding to a sample containing an unknown quantity of a target organism may include a first data subset representing time-series measurement samples of light emitted up to a first point in time in the amplification cycle, the first point in time occurring prior to a peak amplitude of the light emitted over the amplification cycle, a second data subset representing time-series measurement samples of light emitted after the first point in time but before a second point in time in the amplification cycle, the second point in time occurring after the peak amplitude, and a third data subset representing time-series measurement samples of light emitted after the second point in time in the amplification cycle. A computing device configured to receive the first, second, and third data subsets (e.g., computing device 42 of user device 20, a computing device of access point 24, or any other suitable computing device) applies the trained machine learning system to the data subsets (136) and calculates the concentration (e.g., quantity) of the target organism of interest in the sample. In some examples, the computing device then may store one or more such estimated quantities to one or more storage components of a system, such as a memory of an MDS, a memory of a computing device user device 20, a memory of a computing device of access point 24, and/or to any other suitable location.

In some example approaches, the amplitude of light generated early in an amplification cycle (e.g., before phase 94 or phase 104) may be suppressed (e.g., not recorded) so as to not confuse users with background activity. It has been found, however, that such information may be helpful in training the machine learning system. Therefore, in one example approach, the data set includes time-series measurements made before phase 94 in FIG. 6. In a similar example approach, the data set includes time-series measurements made before phase 104 in FIG. 7.

In some example approaches of FIG. 10C, separate machine learning systems are trained as a function of the type of matrix being tested. For instance, a separate system may be trained for testing cheese, or for testing feed, with the parameters of each machine language machine learning system stored in memory based on the type of matrix being tested.

Figure 11:
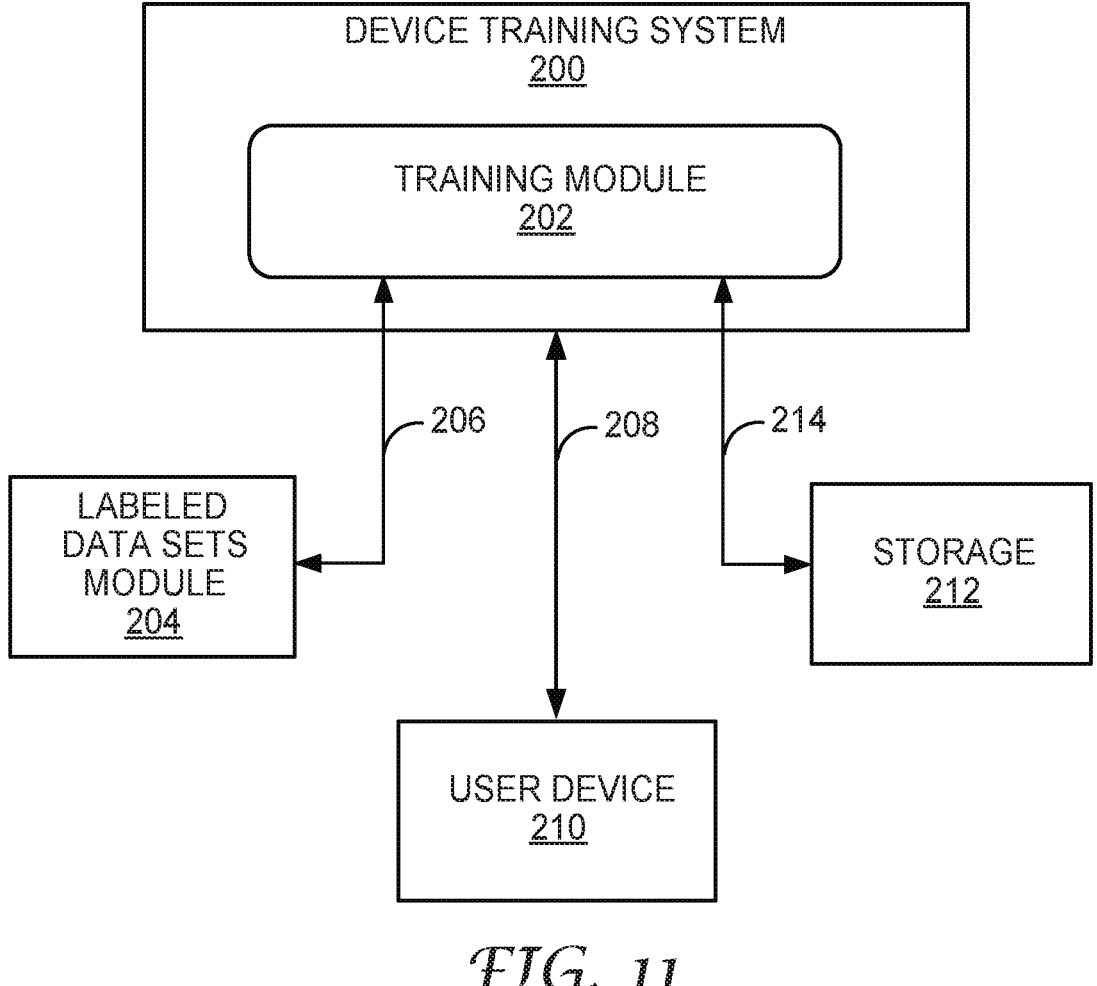
FIG. 11 is a block diagram illustrating a device training system, in accordance with one aspect of this disclosure.

FIG. 11 is a block diagram illustrating a device training system, in accordance with one aspect of this disclosure. In the example shown in FIG. 11, device training system 200 includes a training module 202 connected to labeled data sets module 204 via link 206. In some example approaches, device training system 200 is connected via a link 208 to a user device 210. In one example approach, training module 202 includes a computing device, one or more storage components and a user interface. For example, device training system 200 may include a computing device of external device 28 and memory 32 of FIG. 2. In one example approach, training module 202 receives labeled data sets from labeled data sets module 204. In some such example approaches, each labeled data set is labeled as a false negative data set associated with a biological assay that tested negative for the target nucleic acid due to matrix inhibition or as a true negative data set associated with a biological assay that correctly tested negative for the target nucleic acid. In examples in which the target organism is quantified, the data set includes a target organism quantity associated with a sample and measurements of light detected during an amplification cycle of the sample by a nucleic acid amplification device 8. Training module 202 trains a machine learning system with the labeled data sets and stores parameters associated with the machine learning system in storage 212, which is connected to training module 202 via link 214.

FIGS. 12-25 illustrate example data sets, the application of trained machine-learning systems to such example data sets to detect false negatives, and the results of such applications of trained machine-learning systems to such example data sets. FIGS. 12-15 illustrate an example analysis of a test batch of environmental samples tested for one or more target nucleic acids associated with *Listeria* species, including initial results, application of a matrix control to the initial results, application of a trained machine-learning system to the test batch of samples, and application of the trained machine-learning system that was applied to the test batch of samples to a training data set. FIGS. 16-25 illustrate data sets of a plurality of data sets that was used to train a machine-leaning system, such as the trained machine-learning system applied to the test batch of environmental samples of FIGS. 12-15.

Figure 12:
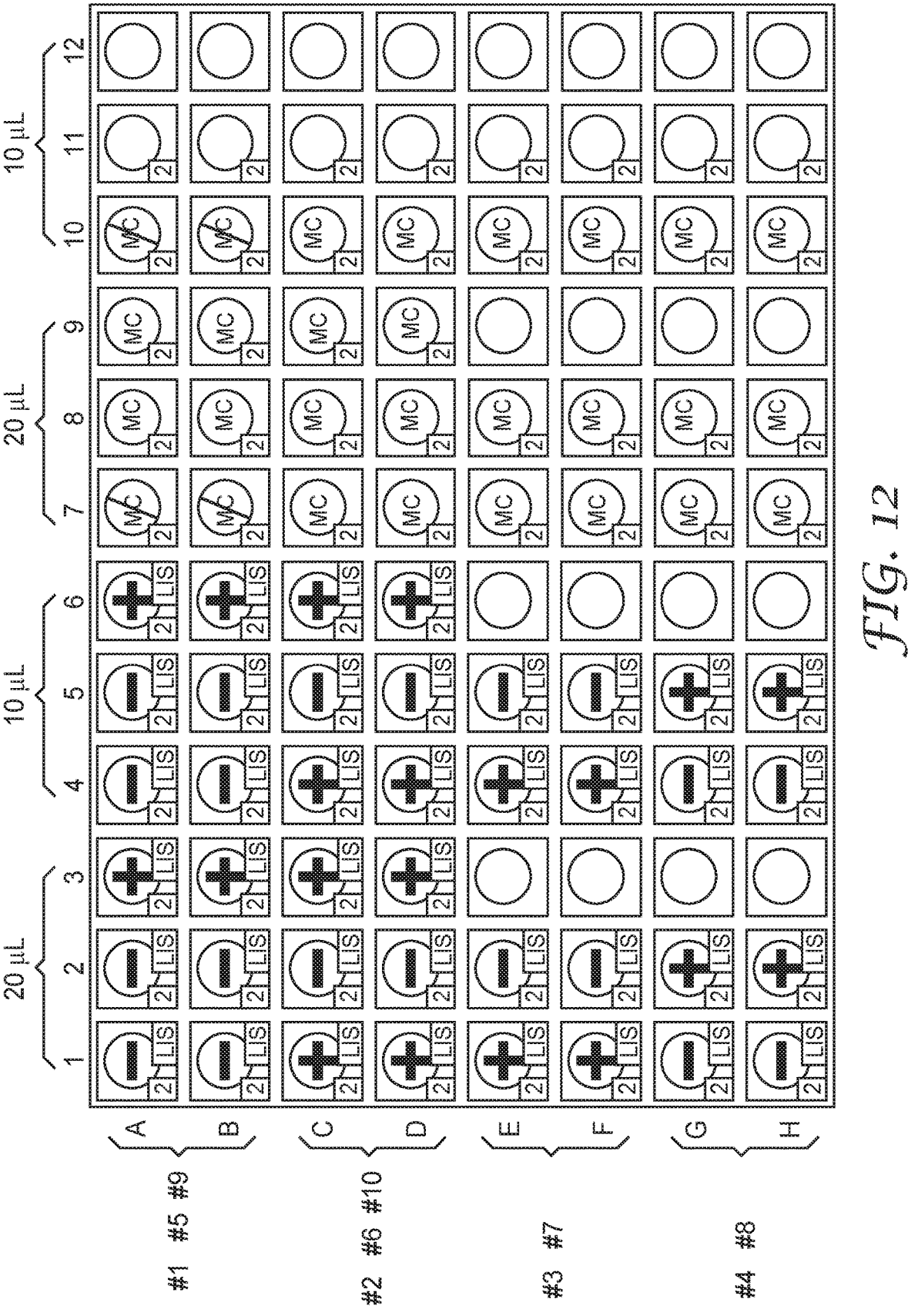
FIG. 12 illustrates an analysis report for environmental samples produced by an example pathogen detection system, in accordance with one aspect of this disclosure.

FIG. 12 illustrates an analysis report for environmental samples produced by an example pathogen detection system, in accordance with one aspect of this disclosure. In the example approach shown in FIG. 12, an example analysis report is associated with a batch of ten environmental samples tested for one or more target nucleic acids associated with *Listeria* species. Such an analysis report may be produced, for instance, by an example pathogen detection system, such as the systems of FIGS. 1 and/or 2, in accordance with one aspect of this disclosure. In the example of FIG. 12, ten samples were analyzed in duplicates using 10 or 20 μL of enrichment broth into a suitable lysis tube. Additional duplicates of each sample were analyzed using an external matrix control to determine inhibitory properties of the samples towards the assay. Samples were loaded starting from A1 in the grid illustrated in FIG. 12 and continuing down the column. The first group in the grid of FIG. 12 corresponds to assays for a target nucleic acid associated with *Listeria* species in which 20 µL of the enriched sample was loaded to the assay. The second group in the grid of FIG. 12 corresponds to *Listeria* species assays from the same enriched samples where 10 µL were loaded. Duplicates of these groups were loaded into the external controls in the third and fourth groups.

During analysis of the batch of ten environmental samples of FIG. 12, Sample #1 was found to be inhibitory to the assay. Determination of Sample #1 as being inhibited was carried out using an external matrix control (labeled as "MC" in FIG. 12), with inhibition of the sample indicated by a slash through the "MC" label associated with Sample #1 in FIG. 12.

Detection software, such as the MDS detection software that produced the analysis report of FIG. 12, may be designed to identify samples as being inhibited when the inhibited matrix control is linked with the sample ID #. Such an approach, however, requires every new sample to be associated with an external matrix control MC and to be labelled accordingly. Since environmental samples vary, this approach may be difficult to apply for a laboratory.

TABLE 3

Results for *Listeria* detection for environmental samples of FIG. 12

| | Result | | | |
|---|---|---|---|---|
| | 20 □L sample to lysis | | 10 □L sample to lysis | |
| Sample ID | MDA 2 LIS | MC | MDA 2 LIS | MC |
| 1 | Negative | Inhibited | Negative | Inhibited |
| 2 | Positive | Valid | Positive | Valid |
| 3 | Positive | Valid | Positive | Valid |
| 4 | Negative | Valid | Negative | Valid |
| 5 | Negative | Valid | Negative | Valid |
| 6 | Negative | Valid | Negative | Valid |
| 7 | Negative | Valid | Negative | Valid |
| 8 | Positive | Valid | Positive | Valid |
| 9 | Positive | Valid | Positive | Valid |
| 10 | Positive | Valid | Positive | Valid |

| | Diluted sample | | | |
|---|---|---|---|---|
| | 20 □l of 1:10 to lysis | | 20 □l of 1:100 to lysis | |
| 1 | Positive | Valid | Positive | Valid |

As in the *Salmonella* example of above, in this example approach, the cultures were serially diluted in Butterfields Buffer and plated onto Petrifilm AC plates following manufacturer's instructions. The cultures were kept at 4-8° C. until plate count results were obtained. The counts obtained were used to estimate the number of cells used for the detection using 3M™ brand Molecular Detection Assay 2—*Listeria* (3M Company) (hereinafter "MDA2—Lis"). A final plate count was conducted using Petrifilm AC plates at the time of conducting the detection assay. These final plate counts were used for reporting the concentration of cells.

In this example run, the external matrix control was not linked to Sample #1 and the detection software falsely labeled Sample #1 as being negative for a target nucleic acid associated with *Listeria* species due to matrix inhibition of the sample. This outcome illustrates one issue with relying only on external matrix controls for detecting inhibition of samples.

Figure 13:
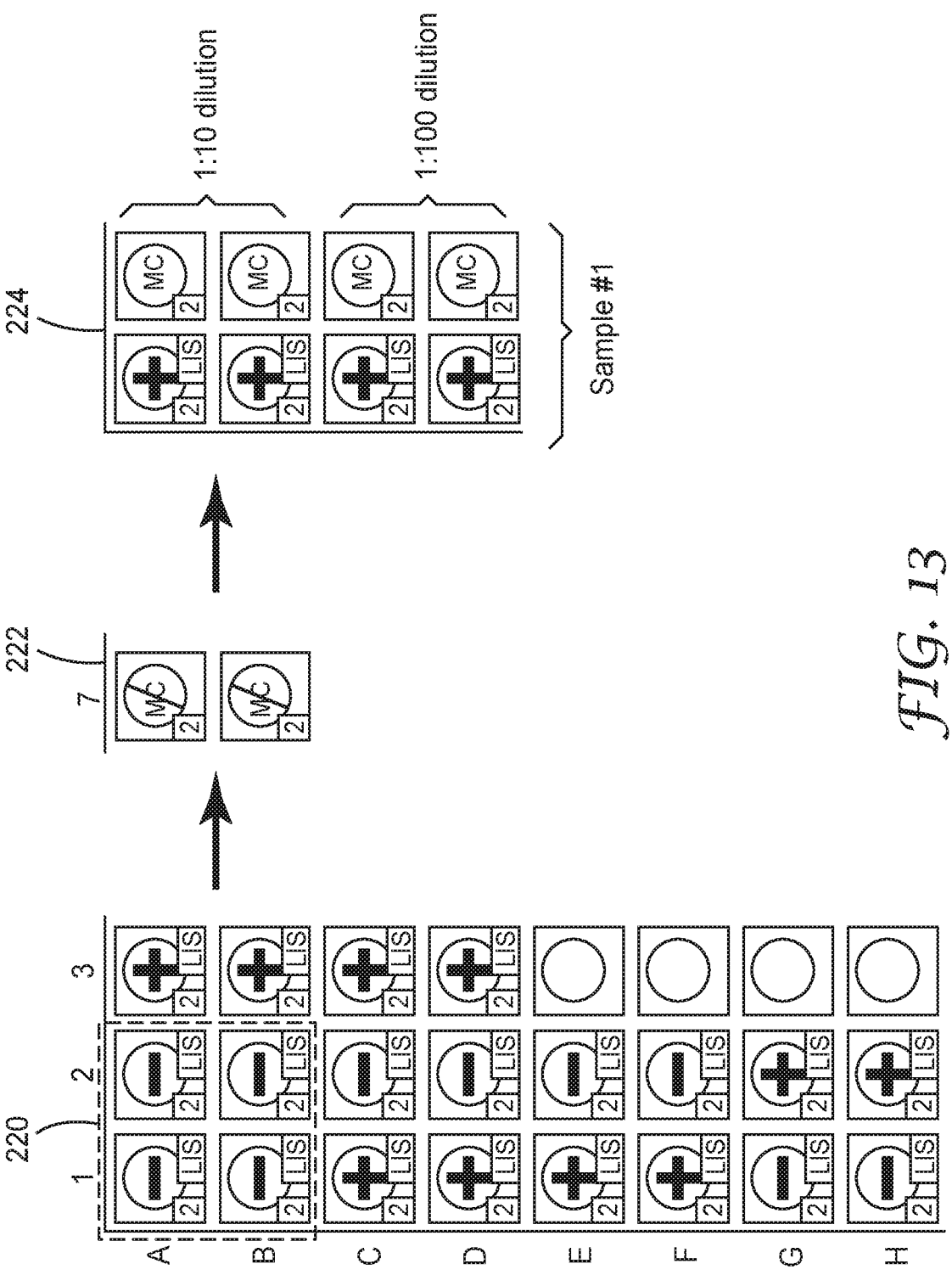
FIG. 13 illustrates a workflow depicting an application of a matrix control and dilution to the samples shown in the analysis report of FIG. 12, in accordance with one aspect of this disclosure.

FIG. 13 illustrates a workflow depicting an application of a matrix control and dilution to the samples shown in the analysis report of FIG. 12, in accordance with one aspect of this disclosure. As discussed above, a user may choose to conduct further analysis of a sample determined to be inhibited (e.g., Sample #1 of FIG. 12), such as to determine whether the target nucleic acid is present in the sample. For example, the sample may be diluted and re-analyzed. Dilution of the sample may help alleviate the inhibitory effect of the matrix, although dilution may also cause loss of signal associated with the target nucleic acid if the initial quantity of the nucleic acid preset in the sample is relatively low. In the example of FIG. 13, Sample #1 (outlined in dashed box 220) was diluted (1:10 and 1:100) in duplicates with corresponding external matrix controls (222) for each replicate. The result of the nucleic acid amplification and detection assay run on the dilution of Sample #1 was positive for *Listeria* species, as shown in FIG. 13 at 224.

Figure 14:
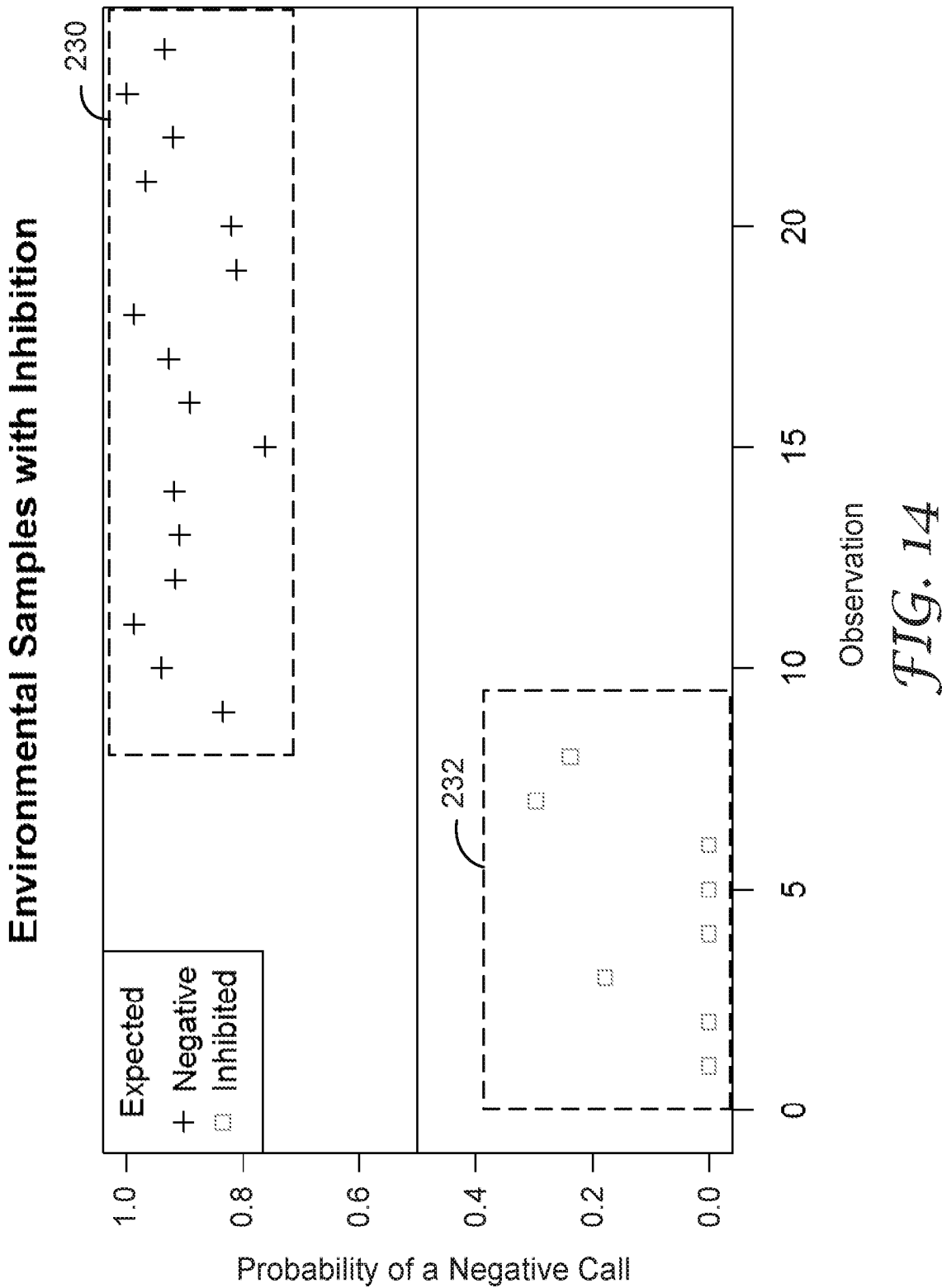
FIG. 14 illustrates results of an application of a trained two-class decision forest algorithm to a collection of data sets, in accordance with one aspect of this disclosure.

FIG. 14 illustrates results of an application of a trained two-class decision forest algorithm to a collection of data sets, in accordance with one aspect of this disclosure. To arrive at the results illustrated in FIG. 14, the samples of FIGS. 12 and 13 were further analyzed using a trained machine-learning system. As illustrated in FIG. 14, the trained machine-learning system was able to discriminate between the true negative results 230 from biological assays correctly identified as testing negative for the target nucleic acid from the false negative results resulting from inhibited biological assays 232. In this example, the trained machine-learning system used was a trained two-class decision forest algorithm trained according to the example technique of FIG. 10A.

Figure 15:
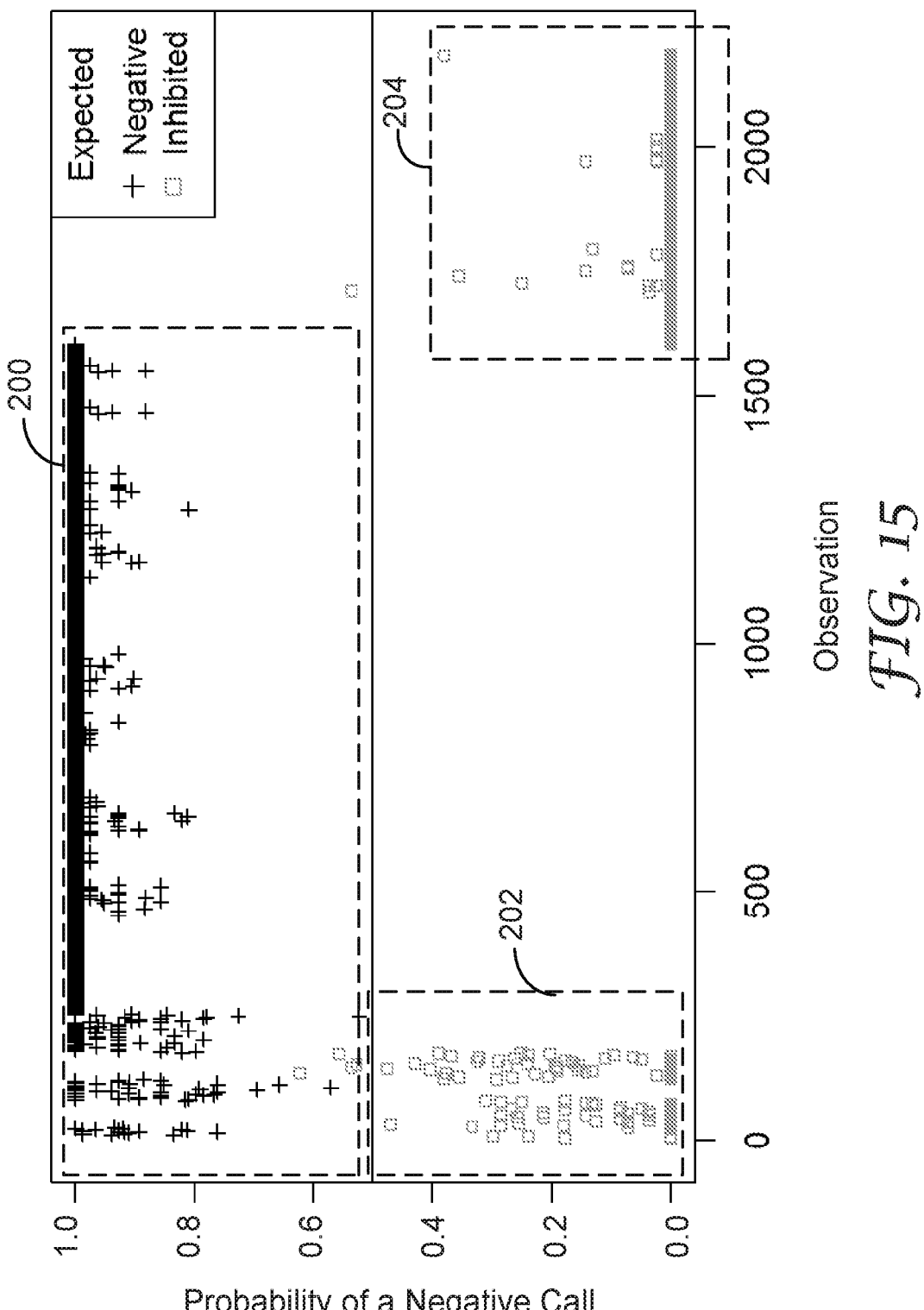
FIG. 15 illustrates results of an application of a trained two-class decision forest algorithm to training data set, in accordance with one aspect of this disclosure.

FIG. 15 illustrates results of an application of the trained two-class decision forest algorithm applied in the example of FIG. 14 to the plurality of training data sets described with respect to the example technique of FIG. 10A. The performance of the trained machine-learning system on the plurality of training data sets is shown in FIG. 15. As noted above in Table 2, the trained two-class decision forest algorithm provided 97.6% accuracy, 97.4% precision, and 99.1% recall when applied to the plurality of training data sets, clustering data sets determined to be true negatives in a cluster 240 as shown near the top of the chart. The algorithm clustered data sets determined to be associated with biological assays that tested negative for the target nucleic acid due to matrix inhibition in clusters 242 and 244 as shown near the bottom of the chart.

Figure 16:
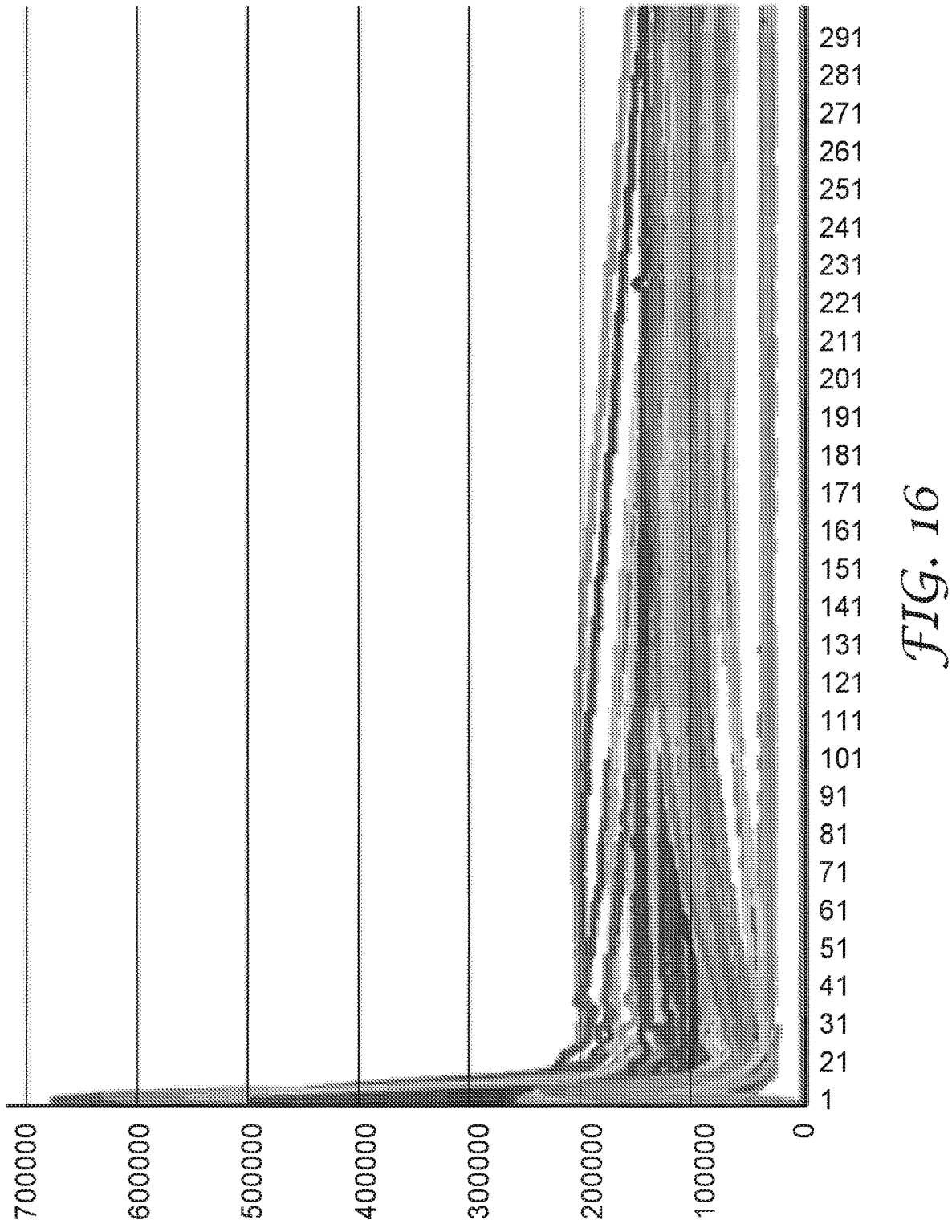
FIG. 16 illustrates an example of a collection of data sets, wherein each data set is represented by a curve representing light intensity over time during one or more nucleic acid amplification cycles, each curve corresponding to a sample, in accordance with one aspect of this disclosure.

FIGS. 16-25 illustrate the application of the machine learning systems of FIGS. 10A-10C to different collections of data sets. FIG. 16 illustrates an example of a collection of data sets, wherein each data set is represented by a curve representing light intensity over time during one or more nucleic acid amplification cycles, each curve corresponding to a sample, in accordance with one aspect of this disclosure. In the examples shown in FIG. 16, each data set follows a curve that reaches a peak before approaching a steady state value of light intensity.

Figure 17:
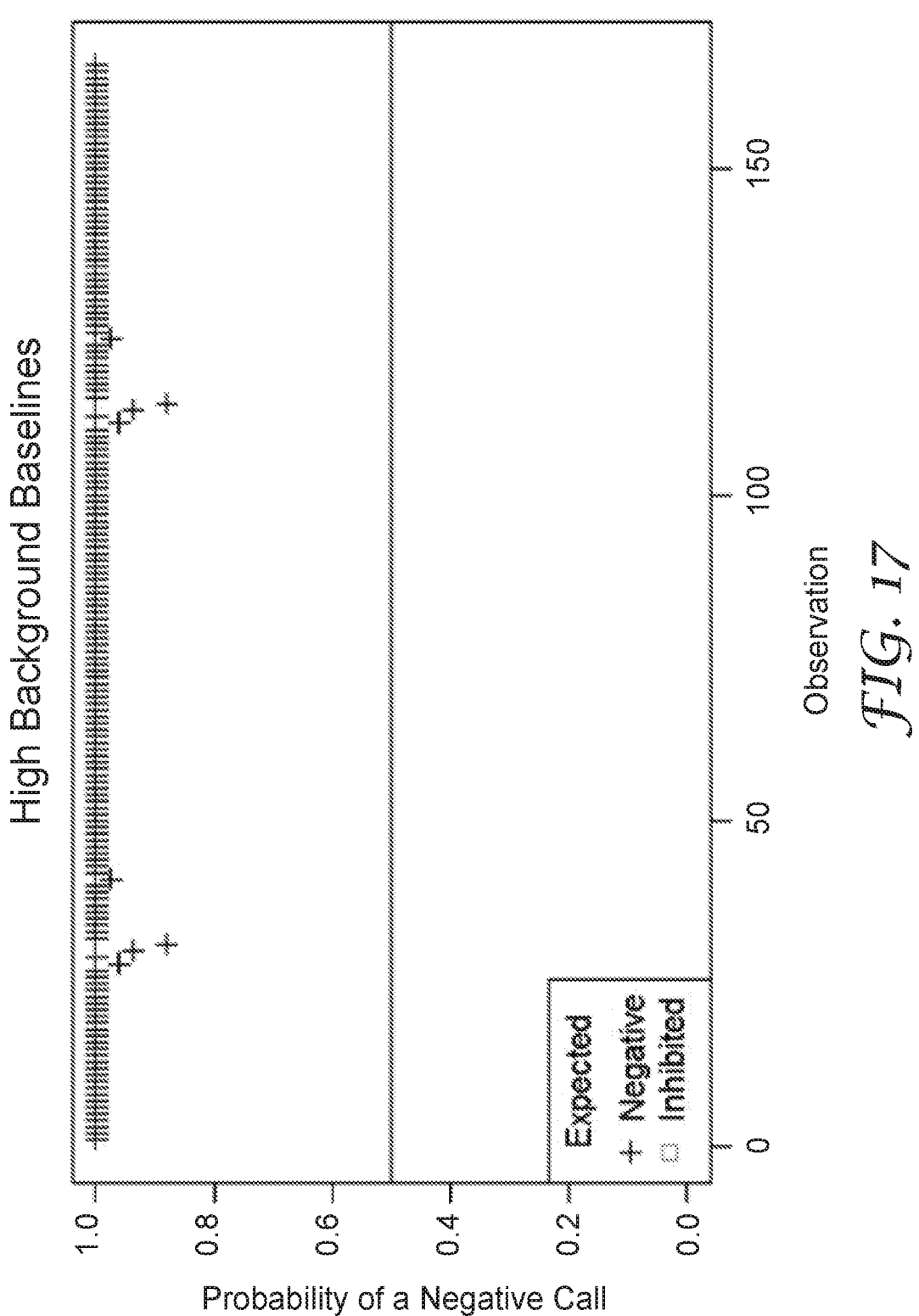
FIG. 17 illustrates results of an application of the trained machine-learning technique of FIGS. 10A-10C (e.g., trained according to the example technique of FIG. 10A) to the data sets of FIG. 16, in accordance with one aspect of this disclosure.

FIG. 17 illustrates results of an application of the trained machine-learning technique of FIGS. 10A-10C (e.g., trained according to the example technique of FIG. 10A) to the data sets of FIG. 16, in accordance with one aspect of this disclosure. As shown in FIG. 17, the trained machine-learning algorithm classified all of the data sets of FIG. 16 as being a true negative (i.e., corresponding to a biological assay in which the target nucleic acid is either not present or not present at above a threshold level) at a relatively high probability.

Figure 18:
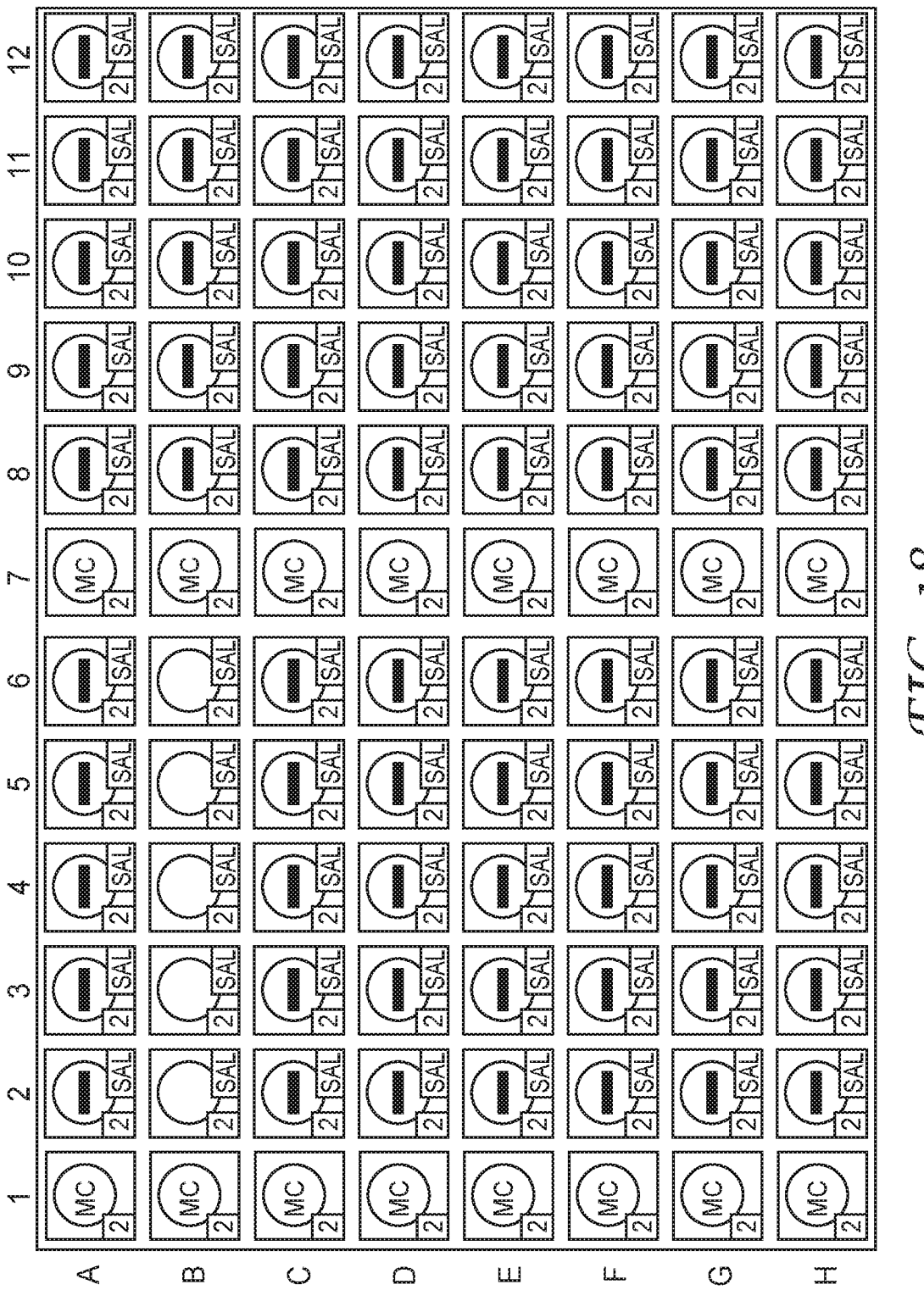
FIG. 18 illustrates an analysis report produced by an example pathogen detection system for a collection of data sets taken from samples associated with matrix ingredients known to be inhibitory, in accordance with one aspect of this disclosure.

FIG. 18 illustrates an analysis report produced by an example pathogen detection system for a collection of data sets taken from samples associated with matrix ingredients known to be inhibitory, in accordance with one aspect of this disclosure. Such matrix ingredients may include compounds such as greases, sanitizers, spices, pigments, enzymes, and other ingredients that may occur within a food, feed, or environmental sample to be tested for a target nucleic acid. The analysis report of FIG. 18 illustrates results for undiluted samples known to be inhibitory (col. 2-6) and corresponding external matrix controls in col. 1 showing inhibition of the assays of col. 2-6. The analysis report of FIG. 18 further illustrates results for dilutions of the samples at col. 8-12 and corresponding external matrix controls in col. 7, showing relief of inhibition of the assays with the exception of the assay corresponding to the sample of row D.

Figure 19:
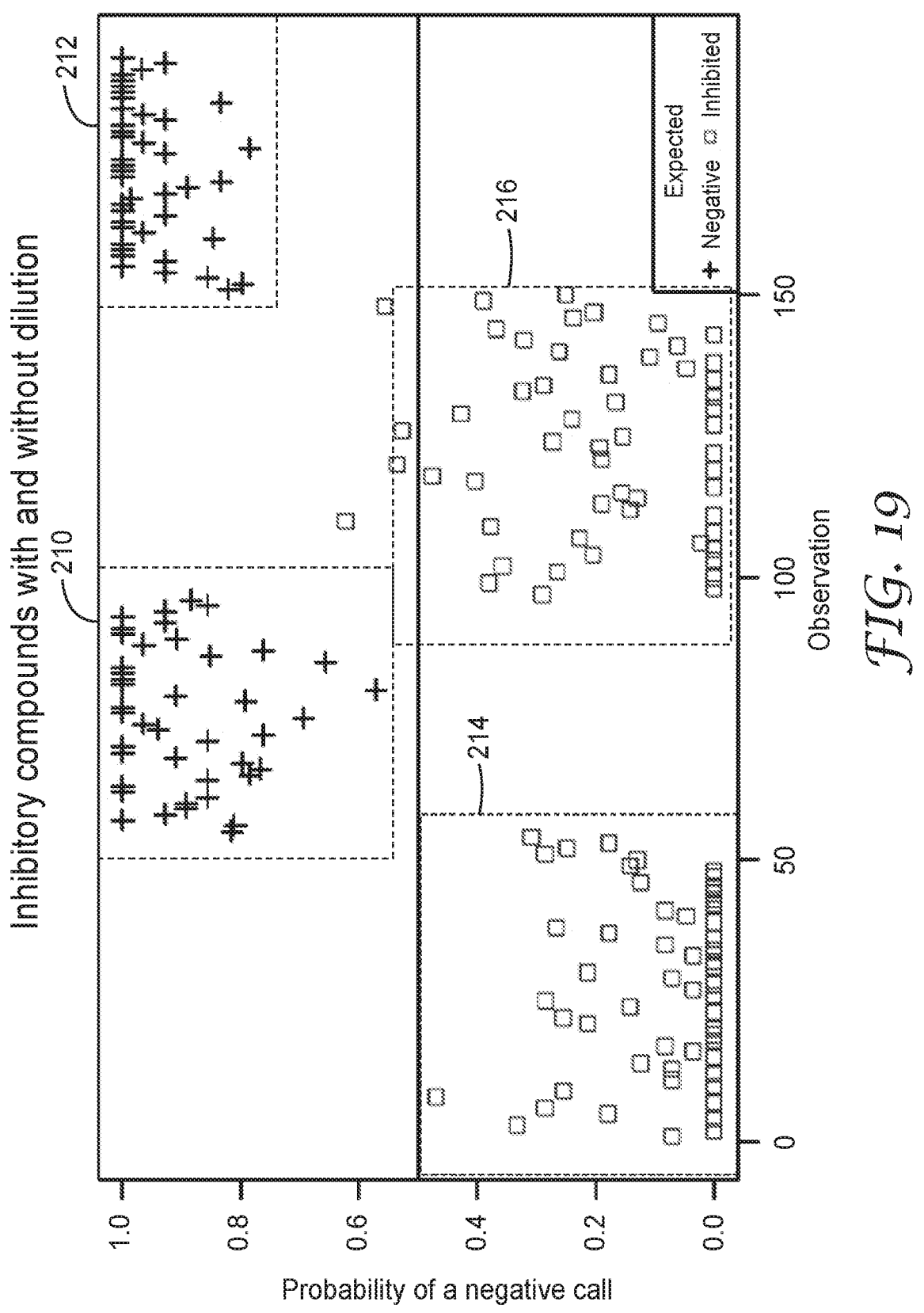
FIG. 19 illustrates results of an application of a trained machine-learning system to the data set of FIG. 18, in accordance with one aspect of this disclosure.

FIG. 19 illustrates results of an application of a trained machine-learning system (e.g., trained according to the example technique of FIG. 10A) to the data sets of FIG. 18, in accordance with one aspect of this disclosure. Clusters 250, 252 of data sets determined to be true negatives (i.e., corresponding to a biological assay in which the target nucleic acid is not present or not present at a threshold level) is shown near the top of the chart. Clusters 254, 256 of data sets determined to be associated with biological assays that tested negative for the target nucleic acid due to matrix inhibition are shown near the bottom of the chart.

Figure 20:
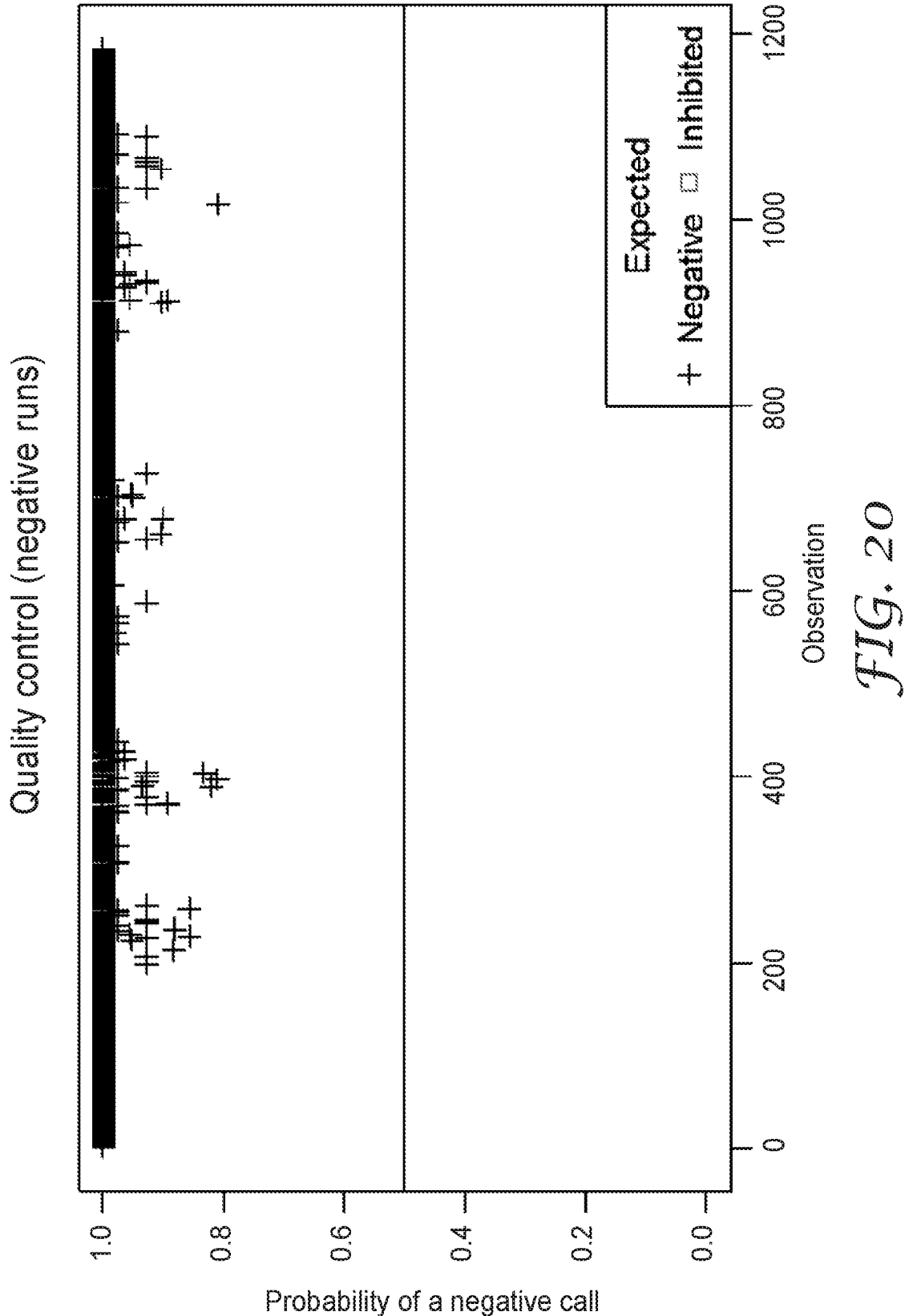
FIG. 20 illustrates an example application of a trained machine-learning system to data sets of quality assurance (QA) laboratory negative control runs, in accordance with one aspect of this disclosure.

FIG. 20 illustrates an example application of a trained machine-learning system to data sets of quality assurance (QA) laboratory negative control runs, in accordance with one aspect of this disclosure. In some example approach, the machine-learning system applied is trained according to the approaches discussed for FIGS. 10A and 10B above. As can be seen in FIG. 20, the trained machine-learning algorithm classified each of the QA lab-negative control runs as being a true negative at a relatively high probability.

Figure 21:
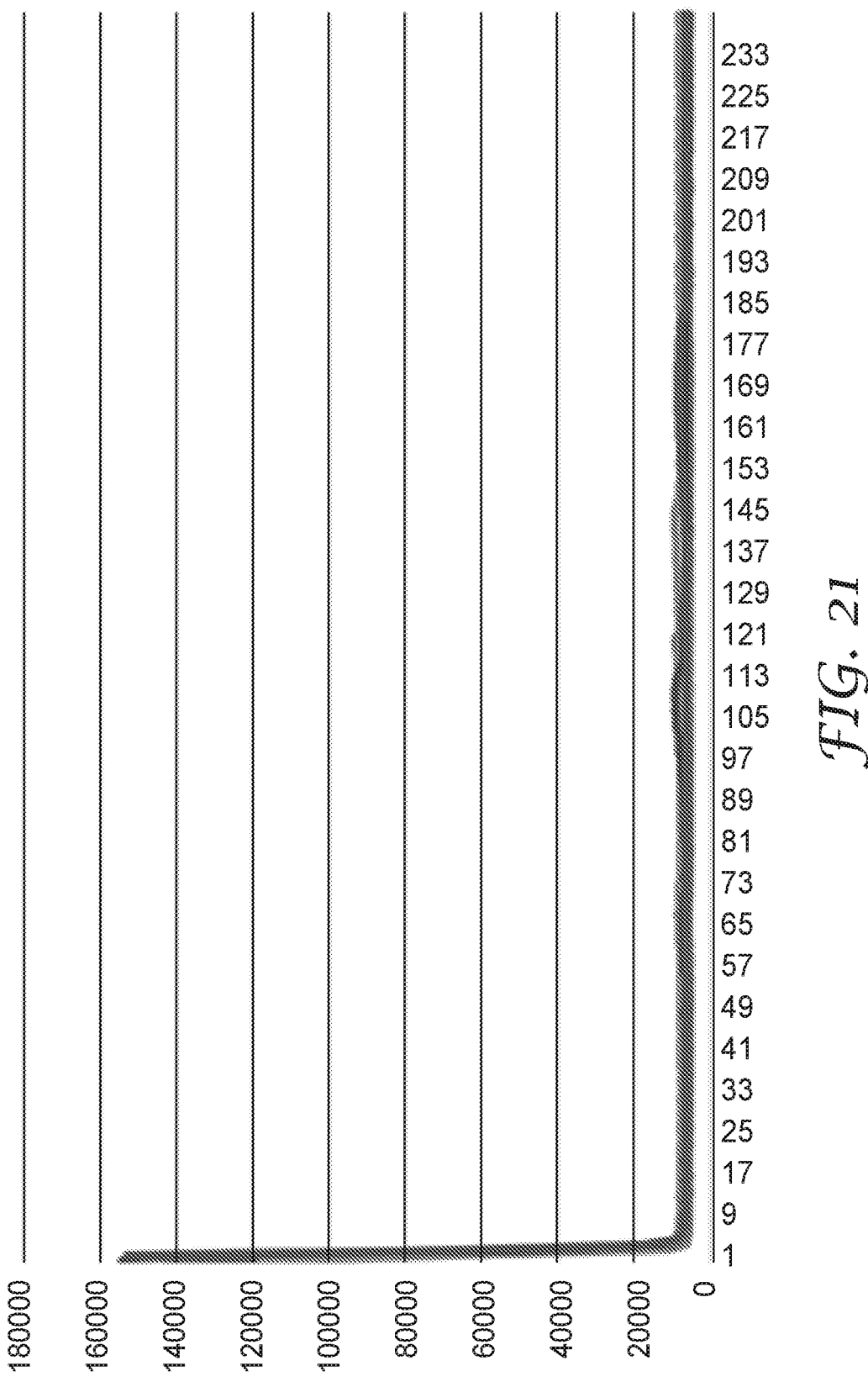
FIG. 21 illustrates an example of a collection of data sets, wherein each data set is represented by a curve representing light intensity over time during one or more nucleic acid amplification cycles, each curve corresponding to a sample known to include an inhibitory matrix resulting in a false negative result.
Figure 22:
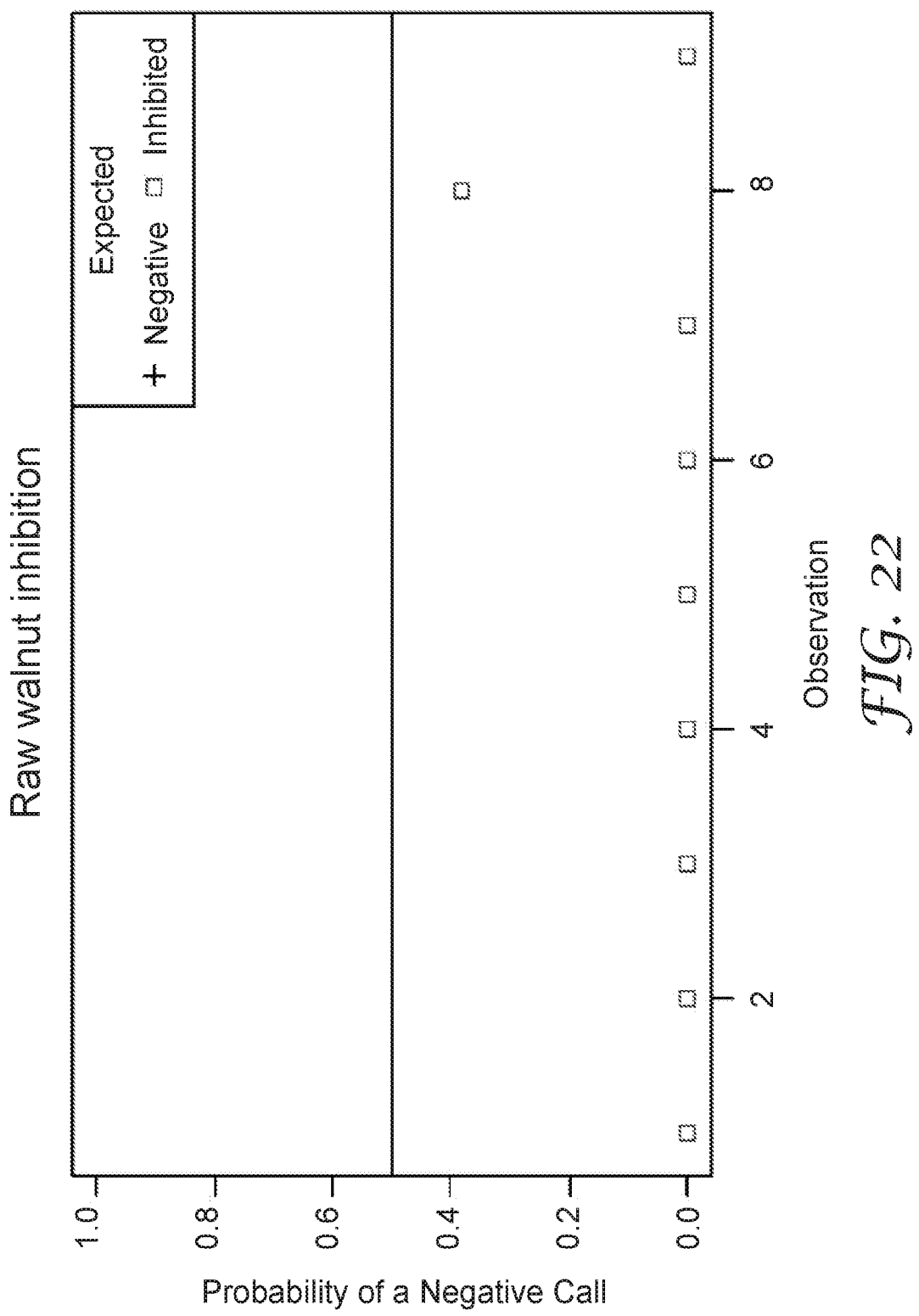
FIG. 22 illustrates an example application of a trained machine-learning system (e.g., trained according to the example technique of FIG. 10C) to the data sets of FIG. 21, in accordance with one aspect of this disclosure.

FIG. 21 illustrates an example of a collection of data sets, wherein each data set is represented by a curve representing light intensity over time during one or more nucleic acid amplification cycles, each curve corresponding to a sample known to include an inhibitory matrix resulting in a false negative result. FIG. 22 illustrates an example application of a trained machine-learning system (e.g., trained according to the example technique of FIG. 10C) to the data sets of FIG. 21, in accordance with one aspect of this disclosure. As illustrated in FIG. 22, the trained machine-learning system validated most of the inhibited samples at a relatively high probability of not being a true negative result (i.e., of being a false negative result and, therefore, corresponding to a biological assay that tested negative for the target nucleic acid due to matrix inhibition).

Figure 23:
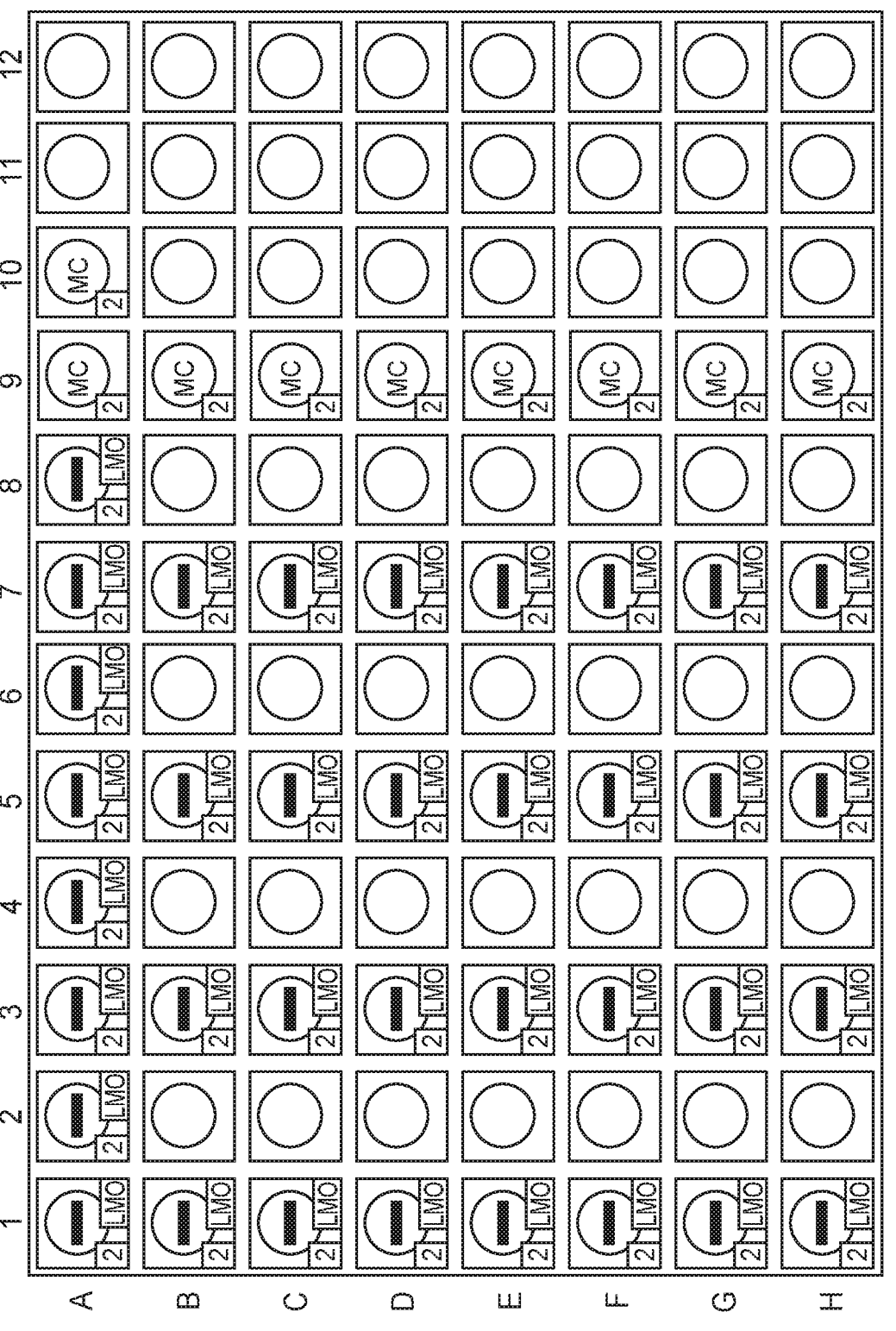
FIGS. 23-25 illustrate application of the machine learning system to data sets from samples containing 6, 7 dihydroxy-coumarin, in accordance with one aspect of this disclosure.
Figure 24:
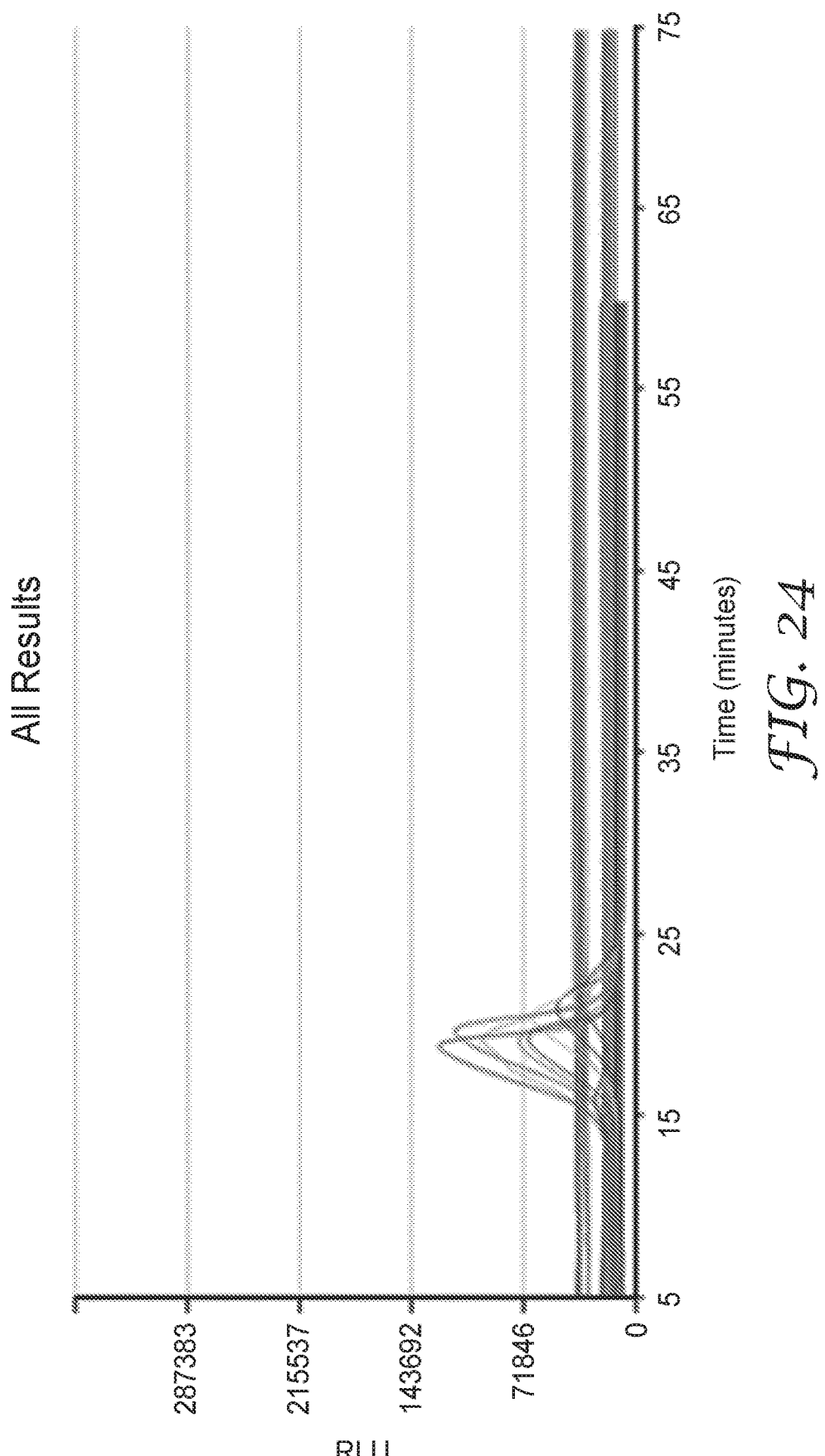
Figure 25:
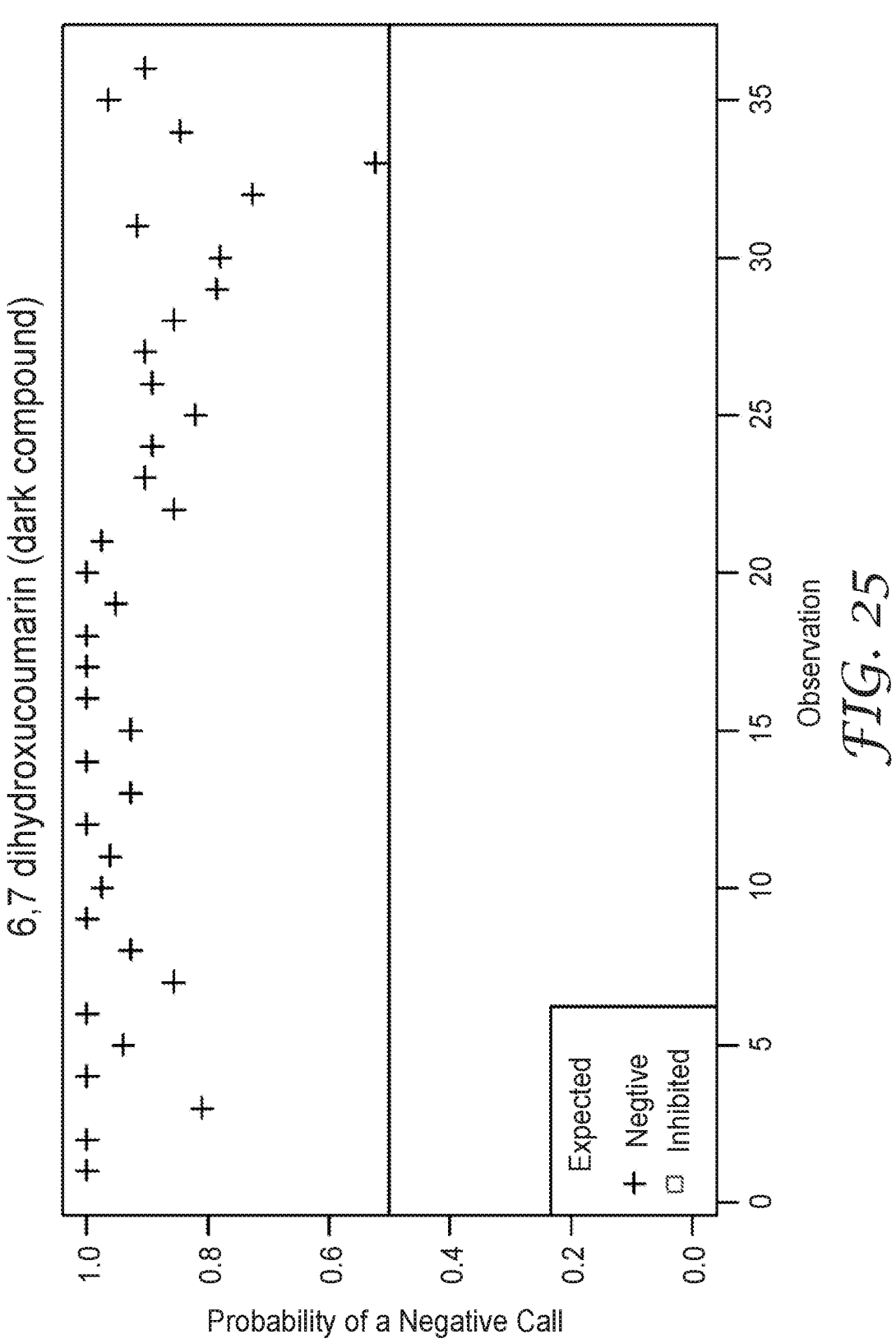

FIGS. 23-25 illustrate application of the machine learning system to data sets from samples containing 6, 7 dihydroxy-coumarin, in accordance with one aspect of this disclosure. FIG. 23, for instance, illustrates an analysis report produced by an example pathogen detection system for a collection of data sets representing nucleic acid amplification cycles performed on samples containing 6, 7 dihydroxycoumarin. As shown in the report of FIG. 23, none of the samples containing 6,7 dihidroxycoumarin were identified as including an inhibitory matrix resulting in a false negative result based on results of corresponding nucleic acid amplification and detection assays.

FIG. 24 illustrates the collection of data sets of FIG. 23, wherein each data set includes a time-series set of measurements of one of the curves for samples shown in FIG. 23, each curve representing light intensity over time during one or more nucleic acid amplification cycles, each curve corresponding to one of the samples containing 6, 7 dihydroxy-coumarin. FIG. 25 illustrates the results of an application of a trained machine-learning system (e.g., trained according to the example technique of FIG. 10C) to the data set of FIG. 23, in accordance with one aspect of this disclosure. As illustrated in FIG. 25, the trained machine-learning algorithm classified most of the samples containing 6, 7 dihy-droxycoumarin as being a true negative result (i.e., corresponding to a biological assay in which the target nucleic acid is not present or not present at a threshold level) at a relatively high probability.

As illustrated generally in FIGS. 14-25, the systems and methods described herein for training and using machine-learning systems may enable such trained machine-learning systems to distinguish between biological assays that truly test negative for a target nucleic acid and biological assays that falsely test negative for the target nucleic acid due to matrix inhibition with generally high levels of accuracy, precision, and recall. Thus, the trained machine-learning systems described herein may help reduce or eliminate the need for the use of internal or external controls with nucleic acid amplification and detection methods such as LAMP. Moreover, the methods for training and using machine-learning systems described herein may utilize background or baseline portions of a reporter (e.g., light) signal in molecular methods for amplifying and detecting a target nucleic acid. In methods other than those described herein, the background or baseline signal is often subtracted from the total reporter signal processing during a DNA amplification technique and little information is obtained from it. Thus, systems and methods described herein may utilize an otherwise unused inherent background or baseline portion of a reporter signal to improve methods of detecting whether a biological assay tested negative for the target nucleic acid due to matrix inhibition in a corresponding sample tested for a target nucleic acid in methods for pathogen detection and/or quantification. Ultimately, such systems and methods may reduce time, cost, and/or complexity of biological assays used for pathogen detection and/or quantification and may help protect consumer health by limiting the release of potentially pathogen-contaminated products.

Various examples have been described. These and other examples are within the scope of the following claims.

What is claimed is:

1. A system for detecting inhibition of a biological assay, comprising:
   a detection device configured to amplify and detect a target nucleic acid associated with a target organism during the biological assay, the detection device comprising:
   a reaction chamber configured to receive a sample comprising a matrix and a quantity of the target nucleic acid and to amplify the target nucleic acid within the sample over a nucleic acid amplification cycle;
   a detector, the detector configured to capture, during the nucleic acid amplification cycle, measurements representative of a quantity of the target nucleic acid present in the sample and to store the measurements in a data set;
   a machine learning system configured to receive the data set, wherein the machine-learning system includes processing circuitry trained to detect biological assays inhibited due to matrix inhibition;
   wherein the machine-learning system is further trained to estimate a quantity of the target organism present in the sample based on measurements present in:

a first data subset, the first data subset including the measurements taken prior to a first point in time, the first point in time occurring prior to a time Tmax, wherein the time Tmax corresponds to a time in the nucleic acid amplification cycle when the measurements reach a maximum amplitude;

a second data subset, the second data subset including the measurements taken after the first point in time but before a second point in time in the nucleic acid amplification cycle, the second point in time occurring after Tmax;

a third data subset, the third data subset including the measurements taken after the second point in time in the nucleic acid amplification cycle;

wherein the nucleic acid cycle has a Tmax;

wherein a data set is comprised of the first data subset, the second data subset, and/or the third data subset;

wherein said data set is analyzed based on said trained machine learning system to estimate the quantity of the target organism in the matrix, and/or to indicate whether a threshold amount of the target organism is present; and in the event that a test is a negative test, said machine learning system is configured to check if said negative test is a false negative.

2. The system of claim 1, wherein the detector measures at least one of bioluminescence, fluorescence, absorbance, transmittance, or reflectance.

3. The system of claim 1, wherein the detector is configured to detect the nucleic acid from at least one of live cells, injured cells, stressed cells, or viable but non-culturable cells.

4. The system of claim 1, wherein the reaction chamber is configured to perform an amplification technique comprising one or more of LAMP, PCR, nucleic acid sequence-based amplification, or transcription-mediated amplification.

5. The system of claim 1, wherein the sample is selected from one of a food, a feed, water or a raw material.

6. The system of claim 1, wherein the sample is an environmental sample from an environment in which at least one of a food, a feed, water or a raw material is harvested, processed, packaged, or used.

7. The system of claim 1, wherein the target organisms are microorganisms of one or more Salmonella species, one or more Listeria species, one or more Campylobacter species, one or more Cronobacter species, one or more E. coli strains, one or more Vibrio species, one or more Shigella species, one or more Legionella species, one or more B. cereus strains, or one or more S. aureus strains, one or more types of viruses, or one or more genetically modified organisms.

8. The system of claim 1, wherein the reaction chamber is further configured to amplify the target nucleic acid in the sample over a plurality of nucleic acid amplification cycles, and wherein the detector is further configured to capture the measurements across the plurality of nucleic acid amplification cycles.

9. The system of claim 1, wherein the machine learning system is based on a regression model.

10. The system of claim 1, where the reaction chamber is further configured to receive a module, wherein the module includes:

a first plurality of reaction vessels, each vessel of the first plurality of reaction vessels containing a quantity of a lysis buffer solution; and a second plurality of reaction vessels, each vessel of the second plurality of reaction vessels containing quantities of one or more reagents configured for use in a nucleic acid amplification reaction.

11. The system of claim 1, wherein said computing device stores the parameters of the trained machine learning system to one or more storage components of a system, wherein said storage components are chosen from a memory of a computing device, user device, and/or a memory of a computing device of access point.

12. A non-transitory computer-readable medium storing instructions that, when executed by processing circuitry, cause the processing circuitry to:

establish a machine-learning system trained to detect matrix-inhibited biological assays;

receive a data set generated by amplifying and detecting a target nucleic acid associated with a target organism in a sample comprising a matrix and a quantity of the target nucleic acid over a nucleic acid amplification cycle, the data set including measurements representative of the quantity of the target nucleic acid present in the sample;

determine, by applying the machine-learning system to the data set, whether the data set is from a matrix-inhibited sample;

label the data set accordingly;

wherein the machine-learning system is further trained to estimate a quantity of the target organism present in the sample based on measurements present in:

a first data subset, the first data subset including the measurements taken prior to a first point in time, the first point in time occurring prior to a time Tmax, wherein the time Tmax corresponds to a time in the nucleic acid amplification cycle when the measurements reach a maximum amplitude;

a second data subset, the second data subset including the measurements taken after the first point in time but before a second point in time in the nucleic acid amplification cycle, the second point in time occurring after Tmax;

a third data subset, the third data subset including the measurements taken after the second point in time in the nucleic acid amplification cycle;

wherein the nucleic acid cycle has a Tmax;

wherein a data set is comprised of the first data subset, the second data subset, and/or the third data subset;

wherein said data set is analyzed based on said trained machine learning system to estimate the quantity of the target organism in the matrix, and/or to indicate whether a threshold amount of the target organism is present; and in the event that a test is a negative test, said machine learning system is configured to check if said negative test is a false negative.

* * * * *